(12) United States Patent
Meador et al.

(10) Patent No.: US 8,314,201 B2
(45) Date of Patent: Nov. 20, 2012

(54) HIGHLY POROUS CERAMIC OXIDE AEROGELS HAVING IMPROVED FLEXIBILITY

(75) Inventors: Mary Ann B. Meador, Strongsville, OH (US); Baochau N. Nguyen, North Royalton, OH (US)

(73) Assignees: The United States of America as represented by the Administration of the National Aeronautics and Space Administration, Washington, DC (US); Ohio Aerosapce Institute, Brookpark, OH (US)

( * ) Notice: Subject to any disclaimer, the term of this patent is extended or adjusted under 35 U.S.C. 154(b) by 1268 days.

(21) Appl. No.: 11/948,315

(22) Filed: Nov. 30, 2007

(65) Prior Publication Data

US 2012/0172475 A1   Jul. 5, 2012

(51) Int. Cl.
*C08G 77/26* (2006.01)
*C08G 77/14* (2006.01)
*C08G 77/28* (2006.01)
*C07F 7/02* (2006.01)

(52) U.S. Cl. ............. 528/28; 528/10; 528/30; 528/38; 423/335

(58) Field of Classification Search .............. None
See application file for complete search history.

(56) References Cited

U.S. PATENT DOCUMENTS

| | | |
|---|---|---|
| 4,374,237 A | 2/1983 | Berger et al. |
| 5,266,207 A | 11/1993 | Boye et al. |
| 5,282,955 A | 2/1994 | Leventis et al. |
| 5,321,102 A | 6/1994 | Loy et al. |
| 5,457,564 A | 10/1995 | Leventis et al. |
| 5,502,082 A | 3/1996 | Unger et al. |
| 5,541,234 A | 7/1996 | Unger et al. |
| 5,605,983 A | 2/1997 | Dauth et al. |
| 5,691,054 A | 11/1997 | Tennent et al. |
| 5,710,187 A | 1/1998 | Steckle, Jr. et al. |
| 5,818,636 A | 10/1998 | Leventis et al. |
| 5,846,658 A | 12/1998 | Tennent et al. |
| 5,872,070 A | 2/1999 | Dismukes et al. |
| 5,990,184 A | 11/1999 | Biesmans et al. |
| 6,080,816 A | 6/2000 | Gregorovich et al. |
| 6,156,812 A | 12/2000 | Lau et al. |
| 6,284,908 B1 | 9/2001 | Loy et al. |
| 6,300,385 B1 | 10/2001 | Hashida et al. |

(Continued)

FOREIGN PATENT DOCUMENTS

WO   2005/079427 A2   9/2005

OTHER PUBLICATIONS

International Search Report and Written Opinion issued Feb. 8, 2012 in related PCT Patent Application No. PCT/US2011/033774.

(Continued)

*Primary Examiner* — Robert S Loewe
(74) *Attorney, Agent, or Firm* — Pearne & Gordon LLP

(57) ABSTRACT

Ceramic oxide aerogels incorporating periodically dispersed flexible linkages are provided. The flexible linkages impart greater flexibility than the native aerogels without those linkages, and have been shown to reduce or eliminate the need for supercritical $CO_2$-mediated drying of the corresponding wet gels. The gels may also be polymer cross-linked via organic polymer chains that are attached to and extend from surface-bound functional groups provided or present over the internal surfaces of a mesoporous ceramic oxide particle network via appropriate chemical reactions.

55 Claims, 13 Drawing Sheets

U.S. PATENT DOCUMENTS

| | | | |
|---|---|---|---|
| 6,364,953 | B1 | 4/2002 | Kawakami et al. |
| 6,423,811 | B1 | 7/2002 | Lau et al. |
| 6,428,898 | B1 | 8/2002 | Barsotti et al. |
| 6,686,035 | B2 | 2/2004 | Jiang et al. |
| 7,470,636 | B2 | 12/2008 | Ko et al. |
| 2002/0167118 | A1 | 11/2002 | Billiet |
| 2003/0106487 | A1 | 6/2003 | Huang |
| 2003/0170386 | A1* | 9/2003 | Gates et al. .............. 427/212 |
| 2004/0005340 | A1 | 1/2004 | Patel et al. |
| 2004/0047988 | A1 | 3/2004 | Lee et al. |
| 2004/0132846 | A1* | 7/2004 | Leventis et al. ............. 521/99 |
| 2004/0144726 | A1 | 7/2004 | Chmelka et al. |
| 2004/0216641 | A1 | 11/2004 | Hamada et al. |
| 2005/0192366 | A1 | 9/2005 | Ou et al. |
| 2005/0192367 | A1 | 9/2005 | Ou et al. |
| 2005/0230298 | A1 | 10/2005 | Jiang et al. |
| 2006/0004121 | A1 | 1/2006 | Ding et al. |
| 2006/0216219 | A1 | 9/2006 | DeFriend et al. |
| 2007/0203341 | A1 | 8/2007 | Shea et al. |
| 2007/0215547 | A1 | 9/2007 | O'Gara |
| 2008/0081120 | A1 | 4/2008 | Van Ooji et al. |
| 2009/0025609 | A1 | 1/2009 | Egami et al. |
| 2009/0036646 | A1 | 2/2009 | Lu et al. |
| 2009/0206034 | A1 | 8/2009 | Nakajima |
| 2010/0003181 | A1 | 1/2010 | Egami et al. |

OTHER PUBLICATIONS

Boday, D.J. et al., "Strong, Low-Density Nanocomposites by Chemical Vapor Deposition and Polymerization of Cyanoacrylates on Aminated Silica Aerogels," Applied Materials & Interfaces, vol. 1, No. 7, pp. 1364-1369, 2009.
Braun, R.D. et al., "Mars Exploration Entry, Descent, and Landing Challenges," Journal of Spacecraft and Rockets, vol. 44, No. 2, pp. 310-323, Mar./Apr. 2007.
Brown, G.J. et al., "Inflatable Aerocapture Decelerators for Mars Orbiters," Paper No. AIAA 2007-2543, 19th AIAA Aerodynamic Decelerator Systems Technology Conference and Seminar, May 21-24, 2007, Williamsburg, VA.
Burchell, M.J. et al., "Capture of Hypervelocity Particles in Aerogel: In Ground Laboratory and Low Earth Orbit," Planetary and Space Science, vol. 47, pp. 189-204, 1999.
Fesmire, J.E., "Aerogel Insulation Systems for Space Launch Applications," Cryogenics, vol. 46, pp. 111-117, 2006.
Gomez Alvarez-Arenas, T.E. et al., "Viscoelasticity of Silica Aerogels at Ultrasonic Frequencies," Applied Physics Letters, vol. 81, No. 7, pp. 1198-1200, Aug. 12, 2002.
Guo, H. et al., "Elastic Low Density Aerogels Derived from Bis[3-(triethoxysilyl)propyl]disulfide, Tetramethylorthosilicate and Vinyltrimethoxysilane via a Two-Step Process," J. Mater. Chem., vol. 19, pp. 9054-9062, 2009.
Jones, S.M., "Aerogel: Space Exploration Applications," J. Sol-Gel Sci. Technol., vol. 40, pp. 351-357, 2006.
Kanamori, K. et al., "New Transparent Methylsilsesquioxane Aerogels and Xerogels with Improved Mechanical Properties," Advanced Materials, vol. 19, pp. 1589-1593, 2007.
Kanamori, K. et al., "Elastic Organic-Inorganic Hybrid Aerogels and Xerogels," J. Sol-Gel Sci. Technol., vol. 48, pp. 172-181, 2008.
Loy, D.A. et al., "Alkylene-Bridged Polysilsesquioxane Aerogels: Highly Porous Hybrid Organic-Inorganic Materials," Journal of Non-Crystalline Solids, vol. 186, pp. 44-53, 1995.
Meador, M.A.B. et al., "Reinforcing Polymer Cross-Linked Aerogels with Carbon Nanofibers," J. Mater. Chem., vol. 18, pp. 1843-1852, 2008.
Meador, M.A.B. et al., "Structure-Property Relationships in Porous 3D Nanostructures: Epoxy-Cross-Linked Silica Aerogels Produced Using Ethanol as the Solvent," Applied Materials & Interfaces, vol. 1, No. 4, pp. 894-906, 2009.
Moner-Girona, M. et al., "Micromechanical Properties of Silica Aerogels," Applied Physics Letters, vol. 75, No. 5, pp. 653-655, Aug. 2, 1999.
Moner-Girona, M. et al., "Mechanical Properties of Silica Aerogels Measured by Microindentation: Influence of Sol-Gel Processing Parameters and Carbon Addition," Journal of Non-Crystalline Solids, vol. 285, pp. 244-250, 2001.
Moner-Girona, M. et al., "Sol-Gel Route to Direct Formation of Silica Aerogel Microparticles Using Supercritical Solvents," J. Sol-Gel Sci. Technol., vol. 26, pp. 645-649, 2003.
Mulik, S. et al., "Cross-Linking 3D Assemblies of Nanoparticles into Mechanically Strong Aerogels by Surface-Initiated Free-Radical Polymerization," Chem. Mater., vol. 20, pp. 5035-5046, 2008.
Mulik, S. et al., "Macroporous Electrically Conducting Carbon Networks by Pyrolysis of Isocyanate-Cross-Linked Resorcinol-Formaldehyde Aerogels," Chem. Mater., vol. 20, pp. 6985-6997, 2008.
Nguyen, B.N. et al., "Tailoring Elastic Properties of Silica Aerogels Cross-Linked with Polystyrene," Applied Materials & Interfaces, vol. 1, No. 3, pp. 621-630, 2009.
Orndoff, E. et al., "Thermal Insulation Performance of Textile Structures for Spacesuit Application at Martian Pressure and Temperature," NASA Document No. 20000040789, 13 pages, 2000.
Parmenter, K.E. et al., "Mechanical Properties of Silica Aerogels," Journal of Non-Crystalline Solids, vol. 223, pp. 179-189, 1998.
Paul, H.L. et al., "Comparison of Thermal Insulation Performance of Fibrous Materials for the Advanced Space Suit," J. Biomechanical Engineering, vol. 125, pp. 639-647, Oct. 2003.
Pekala, R.W. et al., "A Comparison of Mechanical Properties and Scaling Law Relationships for Silica Aerogels and Their Organic Counterparts," Mater. Res. Soc. Symp. Proc., vol. 207, pp. 197-200, 1991.
Pierre, A.C. et al., "Chemistry of Aerogels and Their Applications," Chem. Rev., vol. 102, pp. 4243-4265, 2002.
Rao, A.V. et al., "Synthesis of Flexible Silica Aerogels Using Methyltrimethoxysilane (MTMS) Precursor," Journal of Colloid and Interface Science, vol. 300, pp. 279-285, 2006.
Reza, S. et al., "Aerocapture Inflatable Decelerator (AID) for Planetary Entry," Paper No. AIAA 2007-2516, 19th AIAA Aerodynamic Decelerator Systems Technology Conference and Seminar, May 21-24, 2007, Williamsburg, VA.
Schaefer, D.W. et al., "Structure of Arylene-Bridged Polysilsesquioxane Xerogels and Aerogels," Chem. Mater. vol. 16, pp. 1402-1410, 2004.
Tao, Y. et al., "Conductive and Mesoporous Single-Wall Carbon Nanohorn/Organic Aerogel Composites," Langmuir, vol. 23, pp. 9155-9157, 2007.
Vivod, S.L. et al., "Di-Isocyanate Cross-Linked Silica Aerogels with Hexyl Links Incorporated into the Underlying Silica Backbone," Polymer Preprints, vol. 50, No. 1, pp. 119-120, 2009.
Woigner, T. et al., "Different Kinds of Structure in Aerogels: Relationships with the Mechanical Properties," Journal of Non-Crystalline Solids, vol. 241, pp. 45-52, 1998.
International Search Report and Written Opinion dated Jun. 1, 2009 from corresponding PCT Application No. PCT/US08/80611 (Publication No. WO 2009/073287).
Prosecution history for U.S. Appl. No. 10/643,578.
Prosecution history for U.S. Appl. No. 11/266,025.
Wahab, M.A. et al., "Bridged amine-functionalized mesoporous organosilica materials from 1,2-bis(triethoxysilyl) ethane and bis[(3-trimethoxysilyl)propyl]amine," Journal of Solid State Chemistry, vol. 177, pp. 3439-3447, 2004.
Wahab, M.A. et al., "Periodic Mesoporous Organosilica Materials Incorporating Various Organic Functional Groups: Synthesis, Structural Characterization, and Morphology," Chem. Mater. vol. 17, pp. 2165-2174, 2005.
Armand, A.C., et al., "Caracterisation Acoustique et Mecanique des Aerogels de Silice [Acoustic and Mechanical Characterization of Silica Aerogels]", Journal de Physique IV, Colloque C1, supplement au Journal de Physique III, vol. 2, (1992), C1-759-C1-762.
Bruesch, P., et al., "Electrical and Infrared Dielelectrical Properties of Silica Aerogels and of Silica-Aerogel-Based Composites", Applied Physics A—Solids and Surfaces, (1993), 329-337.
Buttner, D., et al., "Thermal Loss Coefficients of Low-Density Silica Aerogel Tiles", Solar Energy, 40 (1), (1988), 13-15.
Caps, R., et al., "Thermal Transport in Monolithic Silica Aerogel", Revue de Physique Appliquee, Colloque C4, supplement au No. 4, (1989), C4-113-C4-118.
Courtens, E., et al., "Structure and Dynamics of Silica Aerogels", Philosophical Magazine B, 65(2), (1992), 347-355.

Cross, J., et al., "Mechanical Properties of SiO2—Aerogels", Revue de Physique Appliquee, Colloque C4, Supplement au No. 4, (1989), C4-185-C4-190.

Da Silva, A., et al., "Properties of Water Absorbed in Porous Silica Aerogels", Journal of Non-Crystalline Solids, 145, (1992), 168-174.

Damrau, U. et al., "Si MAS-NMR Investigations of Silica Aerogels", Journal of Non-Crystalline Solids, 145, (1992), pp. 164-167.

Devreux, F. et al., "NMR Determination of the Fractal Dimension in Silica Aerogels", Physical Review Letters, 65(5), (1990), pp. 614-617.

Ehrburger-Dolle, F. et al., "Relations Between the Texture of Silica Aerogels and Their Preparation", Journal of Non-Crystalline Solids, 186, (1995), pp. 9-17.

Emmerling, A., et al.., "Relationship Between Optical Transparency and Nanostructural Features of Silica Aerogels", Journal of Non-Crystalline Solids, 185, (1995), pp. 240-248.

Emmerling, A. et al., "Structural Modifications of Highly Porous Silica Aerogels Upon Densification", J. Appl. Cryst., 24, (1991), pp. 781-787.

Gross, J. et al., "Mechanical Properties of SiO2 Aerogels", J. Phys. D: Appl. Phys., 21, (1988), pp. 1447-1451.

Gross, J. et al., "Ultrasonic Evaluation of Elastic Properties of Silica Aerogels", Materials Science and Engineering A., 168, (1993), pp. 235-238.

Gross, J. et al., "Ultrasonic Velocity Measurements in Silica, Carbon and Organic Aerogels", Journal of Non-Crystalline Solids, 145, (1992), pp. 217-222.

Hdach, H. et al., "Effect of Aging and pH on the Modulus of Aerogels", Journal of Non-Crystalline Solids, 121, (1990), pp. 202-205.

Hench, L.L. et al., "The Sol-Gel Process", Chemical Reviews, 90(1), (1990), pp. 33-72.

Hrubesch, L.W. et al., "Thermal Properties of Organic and Inorganic Aerogels", J. Mater. Res., 9(3), (1994), pp. 731-738.

Hrubesch, L.W. et al., "Thin Aerogel Films for Optical, Thermal, Acoustic and Electronic Applications", UCRL-JC-117553 Preprint, International Symposium on Aerogels 4, (Sep. 19-21, 1994 Berkley CA), (Sep. 1994), 17 pgs.

Husing, N. et al., "Aerogels—Airy Materials: Chemistry, Structure and Properties", Angewandt Chemie International Edition, 37, (1998), pp. 22-45.

Jang, K.Y. et al., "Study of Sol-Gel Processing for Fabrication of Hollow Silica-Aerogel Spheres", J. Vac. Sci. Technol. A., 8(3), (May/Jun. 1990), pp. 1732-1735.

Kim, N.K. et al., "Fabrication of Hollow Silica Aerogel Spheres by a Droplet Generation Method and Sol-Gel Processing", J. Vac. Sci. Technol. A. 7(3), (1989), pp. 1181-1184.

Morris, C.A. et al., "Silica Sol as a Nanoglue: Flexible Synthesis of Composite Aerogels", Science, 284, (1999), pp. 622-624.

Novak, B.M. et al., "Low-Density, Mutually Interpenetrating Organic-Inorganic Composite Materials via Supercritical Drying Techniques", Chem. Mater., 6, (1994), pp. 282-286.

Pajonik, G.M., "Some Catalytic Applications of Aerogels for Environmental Purposes", Catalysis Today, 52, (1999), pp. 3-13.

Phalippou, J., et al., "Fracture Toughness of Silica Aerogels", Revue de Physique Appliquee, Colloque C4, Supplement au No. 4, (1989), pp. C4-191-C4-196.

Phallipou, J. et al., "Glasses from Aerogels—Part 1. The Synthesis of Monolithic Silica Aerogels", Journal of Materials Sciences, 25(7), (1990), pp. 3111-3117 allipou, J. et al., "Glasses from Aerogels—Part 1. The Synthesis of Monolithic Silica Aerogels", Journal of Materials Sciences, 25(7), (1990), pp. 3111-3117.

Posselt, D. et al., "The Thermal Conductivity of Silica Aerogels in the Phonon, the Fracton and the Particle-Mode Regime", Europhysics Letters, 16(1), (1991), pp. 59-65.

Rogacki, G. et al., "Diffusion of Ethanol-Liquid CO2 in Silica Aerogel", Journal of Non-Crystalline Solids, 186, (1995), pp. 73-77.

Schaefer, D.W. et al., "Structure and Topology of Silica Aerogels", Journal of Non-Crystalline Solids, 145, (1992), pp. 105-112.

Sleator, T. et al., "Low-Temperature Specific Heat and Thermal Conductivity of Silica Aerogels", Physical Review Letters 66(8), (1991), pp. 1070-1073.

Tsou, P., "Silica Aerogel Captures Cosmic Dust Intact", Journal of Non-Crystalline Solids, 186, (1995), pp. 415-427.

Tullo, A.H., "Stiff Competition—Long Fiber Reinforced Thermoplastics are Gathering Strength in Key Industries", Chem & Eng. News, (Jan. 28, 2002), pp. 21-22.

Woignier, T. et al., "Different Kinds of Fractal Structures in Silica Aerogels", Journal of Non-Crystalline Solids, 121, (1990), pp. 198-201.

Woigner, T. et al., "Glasses from Aerogels. Part 2—The Aerogel-Glass Transformation", (1990), pp. 3118-3126.

Woignier, T. et al., "Mechanical Strength of Silica Aerogels", Journal of Non-Crystalline Solids, 100, (1988), pp. 404-408.

Woigner, T. et al., "Scaling Law Variation of the Mechanical Properties of Silica Aerogels", Revue de Physique Appliquee, Colloque C4, Supplement au No. 4, (1989), pp. C4-179-C4-184.

Woigner, T., et al., "Section 13. Rhelogical, Mechanical and Other Properties—Evolution of Mechanical Properties During the Alcogel-Aerogel Glass Process", Journal of Non-Crystalline Solids, 147 & 148, (1992), pp. 672-680.

Yim, T. J. et al., "Fabrication and Thermophysical Characterization of Nano-Porous Silica-Polyurethane Hybrid Aerogel by Sol-Gel Processing and Supercritical Solvent Drying Technique", Korean J. Chem. Eng. 19(1), (2002), pp. 159-166.

Kramer, S.J., et al., "Organically Modified Silicate Aerogels, Aeromisils", Mat. Res. Soc. Symp. Proc., vol. 435, pp. 295-300, Materials Research Society, 1996.

Katti, Atul, et al., "Chemical, Physical, and Mechanical Characterization of Isocyanate Cross-linked Amine-Modified Silica Aerogels," Chem. Mater., vol. 18, pp. 285-296, American Chemical Society, 2006.

Leventis, Nicholas, et al., "Nanoengineered Silica-Polymer Composite Aerogels with No Need for Supercritical Fluid Drying," Journal of Sol-Gel Science and Technology, vol. 35, pp. 99-105, Springer Science + Business Media, Inc., 2005.

Leventis, Nicholas, et al., "Using Nanoscopic Hosts, Magnetic Guests, and Field Alignment to Create Anisotropic Composite Gels and Aerogels," Nano Letters, vol. 2, No. 1, pp. 63-67, American Chemical Society, 2002.

Meador, Mary Ann B., et al., "Cross-linking Amine-Modified Silica Aerogels with Epoxies: Mechanically Strong Lightweight Porous Materials," Chem. Mater., vol. 17, pp. 1085-1098, American Chemical Society, 2005.

Leventis, Nicholas, et al., "Durable Modification of Silica Aerogel Monoliths with Fluorescent 2, 7-Diazapyrenium Moieties. Sensing Oxygen near the Speed of Open-Air Diffusion," Chem., Mater., vol. 11, pp. 2837-2845, American Chemical Society, 1999.

Zhang, Guohui, et al., "Isocyanate-crosslinked silica aerogel monoliths: preparation and characterization," Journal of Non-Crystalline Solids, vol. 350, pp. 152-164, Elsevier B.V., 2004.

Leventis, Nicholas, et al., "Nanoengineering Strong Silica Aerogels," Nano Letters, vol. 2, No. 9, pp. 957-960, American Chemical Society, 2002.

Hund, Jared F., et al., "Formation and Entrapment of Noble Metal Clusters in Silica Aerogel Monoliths by $\gamma$-Radiolysis," J. Phys. Chem. B, vol. 107, pp. 465-469, American Chemical Society, 2003.

Shea, K.J., et al., "Bridged Polysilsesquioxanes. Molecular-Engineered Hybrid Organic-Inorganic Materials," Chem. Mater., vol. 13, pp. 3306-3319, American Chemical Society, 2001.

Meador, M.A.B., "Structure-Property Relationships in Porous 3D Nanostructures as a Function of Preparation Conditions: Isocyanate Cross-Linked Silica Aerogels." Chem. Mater. 2007, vol. 19, pp. 2247-2260.

Capadona, L.A., et al., "Flexible, Low-Density, Polymer Crosslinked Silica Aerogels", Polymer, 2006, vol. 47, pp. 2247-2260.

Ilhan, U.F., et al., "Hydrophobic Monolithic Aerogels by Nanocasting Polystyrene on Amine-Modified Silica", Mater. Chem., 2006, vol. 16, pp. 3046-3054.

Loy, D.A., et al., "Bridged Polysilsesquioxanes. Highly Porous Hybrid Organic-Inorganic Materials", Chem. Rev., 1995, vol. 95, pp. 1431-1442.

Loy, D.A., et al., "Sol-Gel Synthesis of Hybrid Organic-Inorganic Materials. Hexylene- and Phenylene-Bridged Polysiloxanes", Chem. Mater, 1996, vol. 8, pp. 656-663.

Shea, Kenneth J., et al., "Aryl-Bridged Polysilsesquioxanes—New Microporous Materials", Chemistry of Materials, 1989, vol. 1, pp. 572-574.

Shea, Kenneth J., et al., "A Mechanistic Investigation of Gelation. The Sol-Gel Polymerization of Precursors to Bridged Polysilsesquioxanes", Acc. Chem. Res., 2001, vol. 34, pp. 707-716.

Barton, Thomas J., et al., "Tailored Porous Materials", Chem. Mater., 1999, vol. 11, pp. 2633-2656.

Extended European Search Report issued Jun. 21, 2012 in corresponding European Application No. 08856126.1.

* cited by examiner

HIGHLY POROUS CERAMIC OXIDE AEROGELS HAVING IMPROVED FLEXIBILITY

STATEMENT OF GOVERNMENT-SPONSORED RESEARCH

This invention was made with government support under Contract No. NNC06ZA46A awarded by NASA. The government has certain rights in this invention.

BACKGROUND OF THE INVENTION

1. Field of the Invention

Ceramic aerogels are among the most highly porous and lowest density materials. Their high porosity means that 95% or greater of the total bulk volume of a ceramic aerogel is occupied by empty space (or air), producing excellent thermal as well as sound insulating qualities. In addition, their high specific surface area (e.g. on the order of 600-1000 $m^2/g$) should make them well suited for numerous applications, including as adsorbent beds for chemical separations, as catalyst supports, as platforms for solid state sensors, etc. Unfortunately, conventional ceramic aerogels are physically and hydrolytically very unstable and brittle. Their macro-structure can be completely destroyed by very minor mechanical loads or vibrations, or by exposure to moisture. In addition, over time these materials tend to produce fine particles (dusting) even under no load. Consequently, there has been little interest in ceramic aerogels for the above-mentioned as well as other applications, despite their excellent insulative properties, simply because they are not strong enough to withstand even minor or incidental mechanical stresses likely to be experienced in practical applications.

2. Description of Related Art

U.S. Patent Application Publication No. 2004/0132846, the contents of which are incorporated herein by reference, describes an improvement wherein a diisocyanate is reacted with the hydroxyl groups prevalent on the surfaces of secondary ($\phi$5-10 nm) particles of a silica aerogel to provide a carbamate (urethane) linkage. Additional diisocyanate monomers are further polymerized to produce a network of polyurea chains between the carbamate linkages of respective pairs of hydroxyl groups present on the secondary particles, resulting in a conformal polyurea/polyurethane coating over the silica backbone. The resulting structure was found to have only modestly greater density than the native silica gel (2-3 times greater), but more than two orders of magnitude greater mechanical strength, measured as the ultimate strength at break for comparably dimensioned monoliths.

More recent work has demonstrated that the production of such polymeric conformal coatings is not limited to diisocyanate linkages anchored from surface-native hydroxyl groups. Alternative polymeric architectures have also been shown to produce conformal coatings that dramatically improve the strength of ceramic aerogels. Specifically, non-native functional groups (e.g. amine or vinyl groups) can be incorporated into the surfaces of aerogel secondary particles and used as anchors for other polymeric cross-linking chemistries (such as epoxy and styrene). Methods and chemistries for such alternative polymeric cross-linking architectures are described herein as well as in co-pending, commonly-owned U.S. patent application Ser. No. 11/266,025 and the following publications the contents of all of which are incorporated herein by reference in their entirety:

1. Structure-Property Relationships in Porous 3D Nanostructures as a Function of Preparation Conditions: Isocyanate Cross-Linked Silica Aerogels. Meador, M. A. B.; Capadona, L. A; McCorkle, L.; Papadopoulos, D. S.; Leventis, N., Chem. Mater. 2007, 19, 2247-2260.
2. Flexible, low-density polymer crosslinked silica aerogels. Capadona, L. A., Meador, M. A. B., Alunni, A., Fabrizio, E. F., Vassilaras, P., and Leventis, N. Polymer, 2006, 47, 5754-5761;
3. Chemical, physical and mechanical characterization of isocyanate cross-linked amine modified silica aerogels. Katti, A.; Shimpi, N.; Roy, S.; Lu, H.; Fabrizio, E. F.; Dass, A.; Capadona, L. A.; Leventis, N. Chem. Mater. 2006, 18, 285-296.
4. Cross-linking amine modified silica aerogels with epoxies: mechanically strong lightweight porous materials. Meador, M. A. B., Fabrizio, E. F., Ilhan, F., Dass, A., Zhang, G., Vassilaras, P., Johnston, J. C., and Leventis, N., Chem. Mater., 2005, 17, 1085-1098.
5. Hydrophobic monolithic aerogels by nanocasting polystyrene on amine-modified silica. Ilhan, U. F.; Fabrizio, E. F. McCorkle, L.; Scheiman, D. A.; Dass, A.; Palczer, A.; Meador, M. A. B.; Johnston, J. C. and Leventis, N., J. Mater. Chem., 2006, 16 3046-3054.
6. Bridged Polysilsesquioxanes. Molecular-Engineered Hybrid Organic-Inorganic Materials. Loy, D. A.; Shea, K. J. Chem. Mater. 2001, 13, 3306-3319.
7. Bridged Polysilsesquioxanes. Highly Porous Hybrid Organic-Inorganic Materials. Loy, D. A.; Shea, K. J. Chem. Rev. 1995, 95, 1431-1442.
8. Sol-Gel Synthesis of Hybrid Organic-Inorganic Materials. Hexylene- and Phenylene-Bridged Polysiloxanes. Douglas A. Loy, Gregory M. Jamison, Brigitta M. Baugher, Sharon A. Myers, Roger A. Assink, and Kenneth J. Shea, Chem. Mater. 1996, 8, 656-663
9. U.S. Patent Application Publication No. 2006/021621
10. Aryl-Bridged Polysilsesquioxanes-New Microporous Materials. Kenneth J. Shea* and Douglas A. Loy, Chemistry of Materials 1989, 1, 572-574.
11. A Mechanistic Investigation of Gelation. The Sol-Gel Polymerization of Precursors to Bridged Polysilsesquioxanes. Kenneth J. Shea and Douglas A. Loy Acc. Chem. Res. 2001, 34, 707-716.
12. Tailored Porous Materials. Thomas J. Barton, Lucy M. Bull, Walter G. Klemperer, Douglas A. Loy, Brian McEnaney, Makoto Misono, Peter A. Monson, Guido Pez, George W. Scherer, James C. Vartuli, and Omar M. Yaghi. Chem. Mater. 1999, 11, 2633-2656.
13. U.S. Patent Application Publication No. 2007/0203341
14. U.S. Pat. No. 5,321,102
15. U.S. Pat. No. 6,284,908

The polymer cross-linked aerogels described and referred to above exhibit far greater strength than the corresponding native ceramic aerogels (as much as two orders of magnitude greater strength with only a two- to three-fold increase in density). However, despite their improved strength they still remain relatively inflexible and are subject to brittle failure. Consequently there are numerous applications that could benefit from the insulative and improved mechanical properties of ceramic aerogels as described in the aforementioned publications, but where additional flexibility is necessary or would be desirable. For example, space-suit insulation could benefit significantly from more flexible ceramic aerogels having the insulative properties described above.

Accordingly, it is desirable to produce ceramic oxide aerogels as above, but which exhibit a greater degree of flexibility.

SUMMARY OF THE INVENTION

A ceramic-oxide network is provided, which includes interconnected strands of first particles of ceramic oxide and a plurality of flexible linkages dispersed throughout, but not necessarily uniformly distributed in, that network. The flexible linkages link adjacent ones of the first particles thereby segmenting the interconnected strands. The flexible linkages have the form

-M-L-M- wherein:

M is a metallic or semi-metallic element common to the ceramic oxide network; and L is a flexible linkage between the opposing M atoms that is stable under reaction conditions for synthesizing the ceramic-oxide network.

A method of preparing a ceramic-oxide network is also provided, which includes copolymerizing a reaction mixture that includes at least one ceramic-oxide precursor species and at least one flexible-linkage precursor through one or a series of chemical reactions to produce the ceramic-oxide network. The at least one ceramic-oxide precursor species includes a metallic or semimetallic element bound to at least one moiety through a bond that is labile under conditions of the aforementioned one or a series of chemical reactions. The at least one flexible-linkage precursor has the form $(R)_y(R^1)_x$-M-L-M-$(R^1)_{x'}(R)_{y'}$ wherein:

M is a metallic or semi-metallic element;

each R is attached to the associated M atom via a bond that is labile under the conditions of the aforementioned reaction(s) and is individually selected to be an alkyl, alkoxy or other group that will not prevent that/those reaction(s);

each $R^1$ is attached to the associated M atom via a bond that is not labile under the conditions of the aforementioned reaction(s) and can be individually selected to be an alkyl or other group that will not prevent that/those reaction(s);

L is a flexible linkage between the opposing M atoms that is stable under the conditions of that/those reaction(s);

x and y are both integers with y being not less than 1, wherein the sum x+y is equal to the valence of M minus 1; and x' and y' are both integers with y' being not less than 1, wherein the sum x'+y' is equal to the valence of M minus 1.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Drawings of chemical structures are schematic in nature, are not drawn to scale and are not intended to convey any information regarding the actual number, concentration and/or arrangement of illustrated chemical chains, particles, functional groups, flexible linkages or any other species or portion of a species within a ceramic oxide network. As will be appreciated, the arrangement of these items in the chemical structure drawing figures are for illustrative purposes, and their purpose is simply to schematically illustrate the relationships between the various chemical species, groups, chains and particles as further described herein.

Summary of Sol Gel Chemistry

Aerogels are made by extracting liquid from a solvent-filled gel, to leave behind just a solid-phase three-dimensional network of ceramic oxide particles. The wet gel generally is composed of the solid-phase ceramic oxide network of particles just mentioned, whose vast pore network is filled and occupied by a liquid phase material. The liquid phase material typically comprises or constitutes the solvent, other ancillary species (water, catalyst, initiator, buffer, etc., if present) and any remaining reactant species for forming the network of ceramic oxide particles via the sol gel process. Essentially, one can think of a wet gel and its cognate aerogel as the solvent-saturated solid network of ceramic oxide particles and the dried ceramic oxide network once the solvent has been extracted, respectively.

Figure 1:
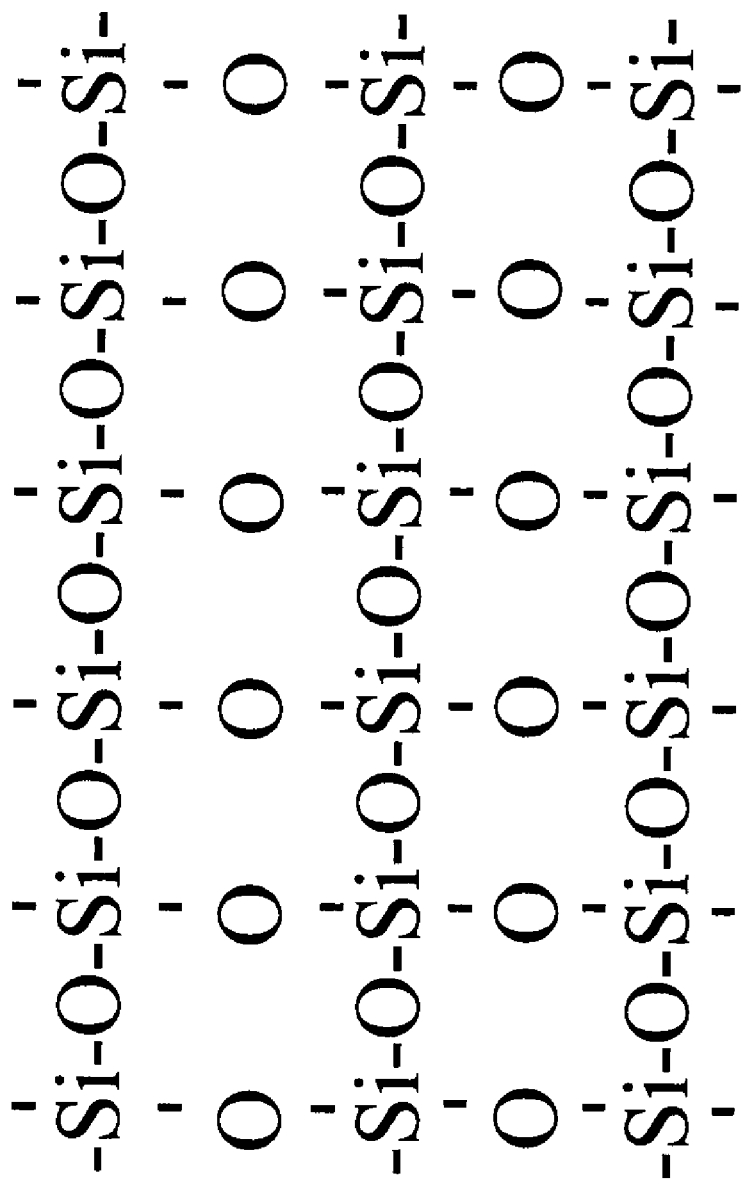
FIG. 1 is a simplified diagram of the structural formula for silica, illustrated in only two dimensions.

A ceramic oxide is an inorganic compound formed between a metallic or a semimetallic element and oxygen; e.g. silica ($SiO_2$), titania ($TiO_2$), alumina ($Al_2O_3$), etc. Generally, a network of ceramic oxide particles comprises a three-dimensional structure, with individual nanoparticles consisting of atoms of the metallic or semimetallic element(s) linked to one another via interposed oxygen atoms. For example, the network structure for silica is illustrated schematically in FIG. 1, though only in two dimensions. Because each silicon atom has four free valences, each is linked to four oxygen atoms. Correspondingly, because each oxygen atom has two donor electron pairs, each of them is linked to two silicon atoms except for oxygen at ceramic particle surfaces, which is linked to one silicon and forms a hydroxyl group. The resulting empirical chemical composition of the nanoparticles is near to $SiO_2$. It will be recognized and understood that other metallic or semimetallic elements having valences other than +4 (such as silicon) will result in correspondingly different chemical compositions in the network of nanoparticles. For example, aluminum has a valence of +3, resulting in the empirical formula $Al_2O_3$ for the corresponding ceramic oxide network. Beyond the foregoing, the only practical constraints for producing a ceramic oxide aerogel are that the metallic or semimetallic element must have a valence of at least, and preferably greater than, +2, and it must be amenable to forming a highly porous three dimensional network of nanoparticles comprising interposed oxygen bonds, e.g. via a sol gel process through reaction of appropriate ceramic oxide precursor species as hereinafter described. Alternatively, other mechanisms for producing such highly porous ceramic oxides can be used.

As evident above, a silica aerogel is prepared by extracting from the pore structure of the solid silica network of nanoparticles the solvent in which that network was made ("gelled"). The three-dimensional network of nanoparticles and the solvent within its pore structure are collectively referred to as a wet gel, also noted above. Briefly, a silica wet gel is made when an alkoxysilane (typically tetramethylorthosilicate or 'TMOS') is hydrolyzed in an appropriate solvent, typically methanol, ethanol, acetone, tetrahydrofuran or acetonitrile, to produce the resulting silica gel network and an alkyl hydroxide byproduct. The byproduct is methanol when TMOS is used. Alternatively, tetraethylorthosilicate or 'TEOS' also can be hydrolyzed to produce a silica gel network, in which case the alkyl hydroxide byproduct will be ethanol. The silica particles are formed through the linkage of silicon atoms in the solution ("sol") via oxygen radicals formed through hydrolysis and condensation. Thus, the silica gel is formed when the nanoparticles become numerous and coagulate against each other into a solid three-dimensional network. The gellation to produce the silica network is a form of cross-linking, wherein silica particles are 'cross-linked' via Si—O—Si linkages in neck regions between particles. However, the term 'cross-link' and cognates thereof are reserved herein for other polymeric linkages between particles that provide a polymeric, cross-linked conformal coating over the secondary particle structure of a ceramic gel as further described herein.

Figure 2:
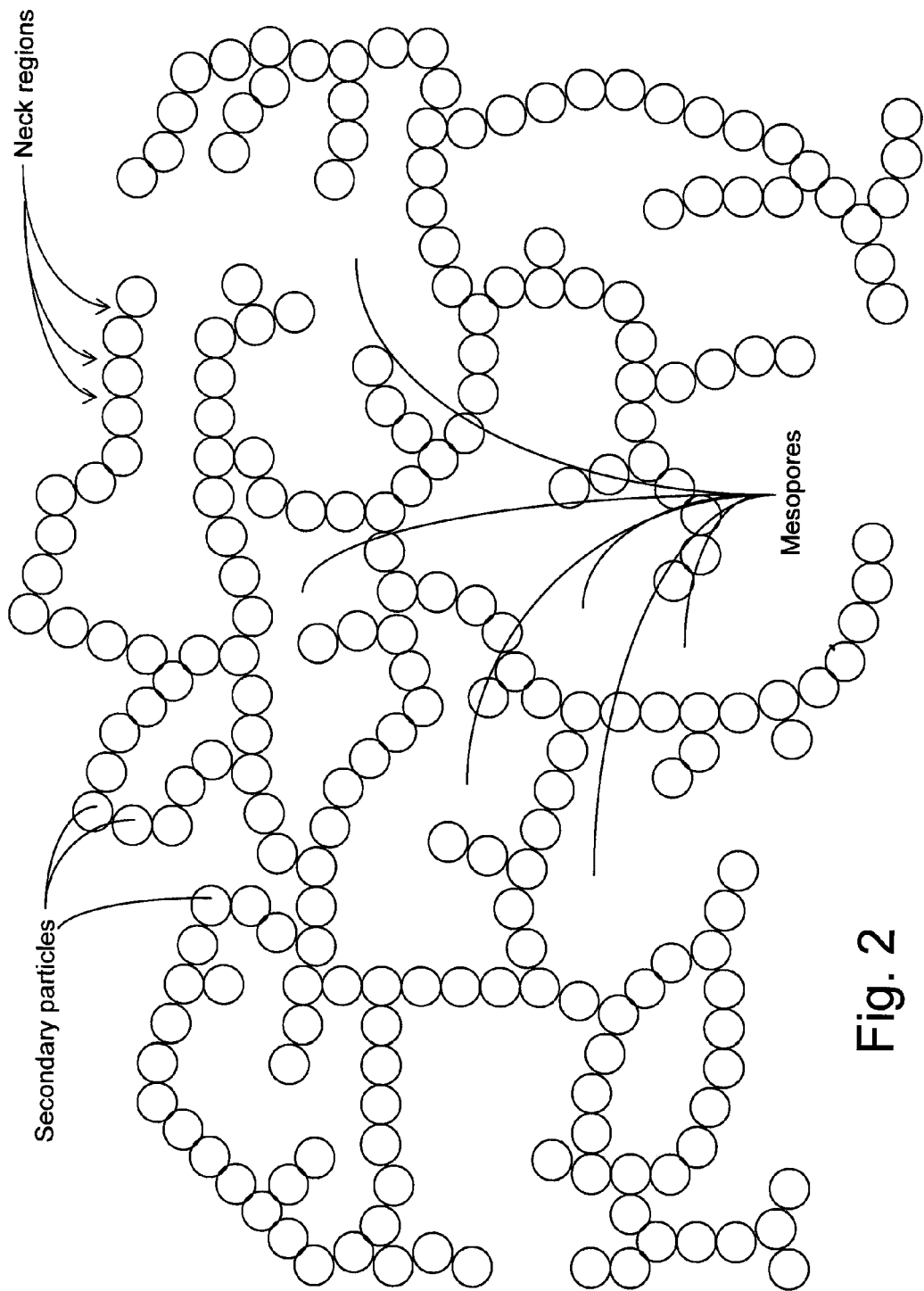
FIG. 2 is a schematic illustration of the structure of a solid silica network, composed of interconnected strands of secondary particles in pearl-necklace configuration.
Figure 3:
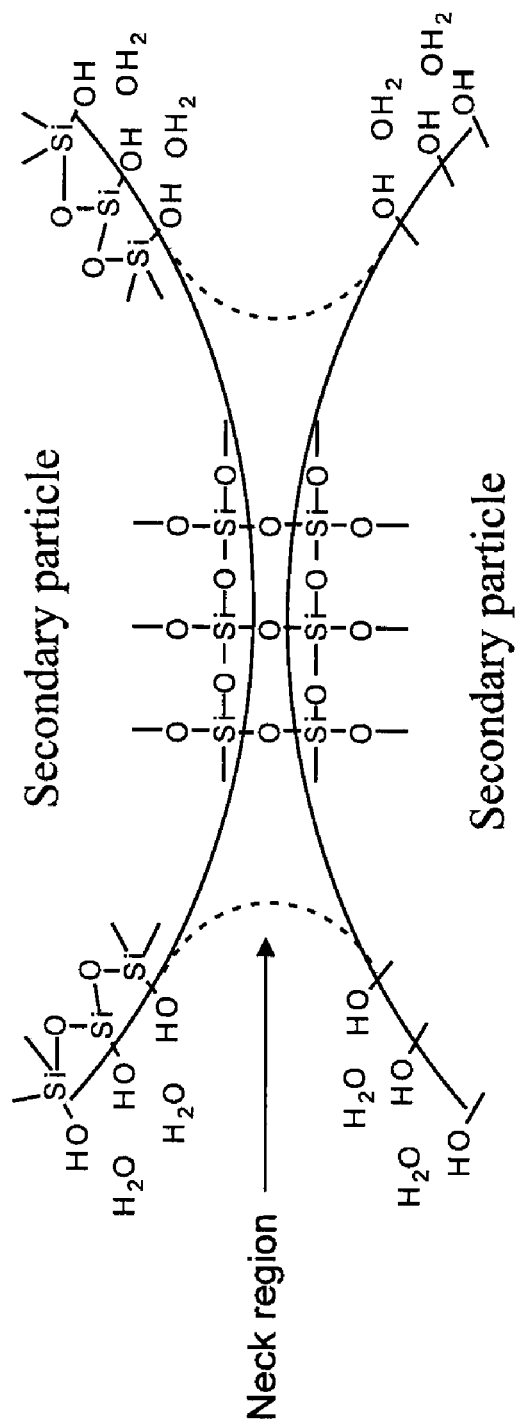
FIG. 3 illustrates two adjacent secondary silica particles linked at a neck region therebetween.

The hydrolysis reaction of the silicon alkoxide is spontaneous, but it occurs too slowly for practical applications (gellation can take days or longer to occur). Hence, it is conventional to employ an acid or a base catalyst, e.g. an amine catalyst, to accelerate the reaction to a more practical rate. On hydrolysis and condensation, the resulting solid silica network is formed having at least two distinct classes or orders of particles, namely primary particles with densities of 1.7 to 2.2 $g/cm_3$ and secondary particles with densities about half of that of the primary particles. The primary silica particles are tightly packed, fully dense solid particles having a particle size of less than 2 nm. The secondary particles have a particle size on the order of 5-10 nm (average particle size greater than 5 nm), and are nanoporous in that they are each made up of an agglomeration of the smaller primary particles. The nanopores in the secondary particles are provided as the space between the agglomerated primary particles that make up each secondary particle. The secondary particles are arranged to provide an interconnected network of long strands of the secondary particles to form a mesoporous structure as illustrated in FIG. 2. The secondary-particle strands are often referred to and known as a "pearl necklace" configuration. Within each such strand, secondary particles are linked with adjacent particles via Si—O—Si bonds across relatively narrow 'neck regions' between the particles as shown in FIG. 3. The empty space between the pearl necklace strands of secondary particles is referred to as mesoporosity and accounts for up to 95% of the total volume of the solid network's macrostructure, which is what affords these gels their desirable properties.

Once the solid silica network is formed, it is necessary to extract the solvent from the pore system (meso- and nanopores) of the solid network. Historically, this had been difficult to achieve while maintaining the structural integrity of the silica gel due to the presence of the mesopores in the solid network. The liquid-vapor interface produced on evaporation of liquid within the mesopores would exert strong surface tension forces that cause the collapse of the pore structure, causing the solid gels to fracture or shrink, often considerably compared to their initial size and form. To solve this problem, the solvent in the pore system of a silica wet gel is traditionally exchanged with liquid carbon dioxide above its vapor pressure. The resulting sol gel, now having liquid $CO_2$ in the pore system, is heated and pressurized beyond the critical temperature and pressure of $CO_2$, thus supercritically gasifying the $CO_2$ within the pore system of the solid gel network all at once. The supercritical carbon dioxide is vented, leaving behind the solid silica gel network thereby producing a dried silica aerogel whose physical structure is substantially unchanged and undamaged compared to the parent wet gel form. Converting the liquid $CO_2$ directly into supercritical $CO_2$ prior to venting results in there never being a liquid-gas interface in the mesopores of the gel; hence no surface tension forces are exerted on the pore surfaces and the solid structure remains intact. An alternative method for drying aerogels to limit shrinkage is solvent exchange with a low-surface-interactive solvent, such as pentane or fluorinated solvents. The solvent-exchange occurs progressively over several washings with increasing concentration of the low-surface-interactive exchange solvent for each washing. Once the solvent has been completely exchanged with such a low-surface-interactive solvent, the gel is removed and permitted to dry. This method should work best with aerogels that have been made somewhat hydrophobic. Styrene polymer-cross-linked gels (as described below) should be able to be dried in this way. One paper reports that this latter method can be practiced with isocyanate polymer-cross-linked gels (Leventis, Palczer, McCorkle, Zhang, Sotiriou-Leventis, *J. Sol-Gel Sci. Technol.* 2005, 35, 99-105), although it has not been found to provide very reproducible results in practice.

The supercritical $CO_2$ or solvent-exchange drying methodologies described here (principally the $CO_2$ method) have remained necessary even for ceramic aerogels that include a conformal polymer cross-linked coating as described above in order to prevent or minimize shrinkage or collapse of the wet gels when drying to produce aerogels. As will be explained below, the introduction of a degree of flexibility into the secondary-particle skeleton of such gels may further reduce or eliminate the need for supercritical $CO_2$-mediated drying (or solvent-exchange methodologies described above, which have shown limited effectiveness) of the wet gels, which are costly and time-consuming.

DETAILED DESCRIPTION OF PREFERRED EMBODIMENTS

As used herein, whenever a range such as 5-25 (or 5 to 25) is given, this means preferably at least 5 and, separately and independently, preferably not more than 25.

A degree of additional flexibility can be imparted to ceramic aerogels via incorporation of flexible organic linkages between adjacent secondary particles in the mesoporous ceramic oxide network. This structure is illustrated schematically in FIG. 4. As can be seen in the figure, the ceramic oxide network is essentially the same as that in FIG. 2, except that flexible linkages (illustrated schematically as 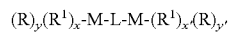) have been interposed periodically between adjacent secondary particles, thereby segmenting the secondary-particle strands. By 'periodically,' it is meant that the flexible linkages described here are dispersed throughout the secondary-particle network, not necessarily uniformly distributed or provided at regular intervals or periods, but at a relative frequency or 'concentration' based on the molar ratio of the flexible linkage precursor species relative to other ceramic oxide precursors that go into forming the ceramic oxide network, as will be further described. The interposition of these organic chains in between adjacent secondary particles in the ceramic oxide network, it is believed, has the effect of segmenting (i.e. breaking up or shortening) the 'pearl-necklace' strands of secondary particles, which are otherwise quite rigid based on their attachment within the neck regions as shown in FIG. 3. Specifically, the flexible linkages are believed to be more flexible than the direct particle-to-particle linkages that otherwise form between adjacent secondary particles in a ceramic oxide network, and to impart greater flexibility between shorter strands of pearl-necklace-configured secondary particles. The overall result is to produce a ceramic gel that exhibits a greater degree of flexibility than a native gel lacking interposed flexible linkages, whether or not the gel includes a polymeric cross-linked conformal coating as mentioned above and described more fully below.

The ceramic oxide aerogels with improved flexibility will be best understood through a description of a method by which they can be made.

A ceramic oxide network (whether or not functionalized with non-hydroxyl groups) is prepared preferably through a sol gel process. To introduce any desired non-hydroxyl functionality to the ceramic oxide, a functionalized ceramic oxide precursor that is compatible with sol gel chemistry to produce a solvent-filled gel of ceramic oxide network particles via a chemical reaction is copolymerized with an unfunctionalized ceramic oxide precursor via that reaction to produce the particle network. As used herein, an unfunctionalized ceramic oxide precursor is a species composed of a metallic or semi-metallic element bound to other moieties all through bonds that are labile and subject to being broken under the conditions of the particular reaction that is or will be used to produce the ceramic oxide particle network of the wet gel (sol gel process); i.e. reaction-labile bonds. Conversely, a functionalized ceramic oxide precursor is a species composed of a metallic or semimetallic element that is bound to at least one non-hydroxyl functional group via a bond that is not labile (not subject to being broken) under those reaction conditions (i.e. non-reaction-labile), in addition to at least one, preferably more than one, other moiety via a bond that is labile under those conditions. As the particular chemical reaction proceeds, the solid network of nanoparticles is formed through copolymerization of both the unfunctionalized and any functionalized (if present) precursor species to produce a ceramic oxide wet gel having the desired non-hydroxyl functional groups (if any) attached to the network, in addition to the surface-bound hydroxyl groups that are native to ceramic oxides. As will be seen, at least a portion (probably a significant proportion) of the non-hydroxyl functional groups are surface-bound on the secondary ceramic oxide particles, probably displacing (taking the place of) a proportionate number or quantity of hydroxyl groups. Methods and species to introduce such non-hydroxyl functional groups will be more fully described below.

To provide flexibility to the resulting ceramic oxide gels, both wet and in the dried aerogel form, a precursor for a flexible linking species (sometimes referred to herein as a "flex link") precursor having the following general structure is incorporated into the reaction mixture prior to the gel-synthesis reaction described above:

$$(R)_y(R^1)_x\text{-M-L-M-}(R^1)_{x'}(R)_{y'}$$

wherein:
M is a metallic or semi-metallic element common to the ceramic oxide network (e.g. Si for an $SiO_2$ network, Al for an $Al_2O_3$ network, etc.);
each R is attached to the associated M atom via a bond that is labile under the conditions of the reaction(s) that is or will be used to produce the ceramic oxide particle network from the ceramic oxide precursors (functionalized or unfunctionalized), and wherein each R can be individually selected to be any alkyl, alkoxy or other group that will not impermissibly interfere with or prevent the aforesaid reaction(s);
each $R^1$ is attached to the associated M atom via a bond that is not labile under the above-mentioned reaction conditions and can be individually selected to be an alkyl group or any other group that will not impermissibly interfere with or prevent the aforesaid reaction(s);
L is a flexible linkage between the opposing M atoms that can have any suitable form that is stable under the network-synthesis reaction conditions;
x and y are both integers with y being not less than 1, wherein the sum x+y is equal to the valence of M minus 1; and
x' and y' are both integers with y' being not less than 1, wherein the sum x'+y' is equal to the valence of M minus 1.

The R groups described above are termed leaving groups because they leave the associated M atom once the reaction-labile bond therebetween is severed; i.e. under the reaction conditions for synthesizing the network. The $R^1$ groups (if present) are retained with the associated M atoms, and therefore in the resulting network, because the bonds therebetween are not labile and thus not broken under the reaction conditions. During the reaction that forms the ceramic oxide network from the ceramic oxide precursor species, the reaction-labile bonds between the R (leaving) groups and M atoms in the flex link precursor are severed, and the resulting {-M-L-M-} linking species (with $R^1$s if present) is incorporated into the forming ceramic oxide network. It is to be noted that each such M may be linked to the ceramic oxide network via multiple bonds; i.e. up to y or y' bonds depending on the particular M atom.

In one embodiment, x and x' are both zero, and the formula for the flexible-linkage precursor reduces to $(R)_y$-M-L-M-$(R)_{y'}$ wherein y is between 1 and the valence of M minus 1. As described more fully below, it has been found that ceramic oxide aerogels prepared according to this methodology and using such exhibit a surprising degree of flexibility, both in the wet gel and dried aerogel states, and provide improved green strength for wet gels prior to polymer cross-linking via surface-bound functional groups as more fully described below.

The ceramic gels (wet gels and dried aerogels) with improved flexibility and processes for making them, described above in summary, will now be more fully described primarily with respect to the preparation of a flexible silica aerogel. However, it will be understood by persons of ordinary skill in the art that other ceramic oxides can be used based on selection of appropriate ceramic oxide precursor species, as well as flex link precursors, that can be reacted to produce a corresponding flexible ceramic oxide network based on another metallic or semimetallic atom, e.g. Al, V, Ti, Zr, etc.

To prepare a flexible silica aerogel, first the corresponding silica wet gel is prepared. Silica wet gels are prepared by hydrolyzing an alkoxysilane such as TMOS and TEOS to produce the wet gel having a solid silica particle network similarly as described above. TMOS or TEOS are unfunctionalized ceramic oxide ($SiO_2$) precursors, wherein all moieties attached to the central Si atom (methoxy for TMOS, ethoxy for TEOS) are attached via a reaction-labile bond, i.e. a hydrolysable bond based on the reaction mechanism by which $SiO_2$ gels are prepared. As used herein, a hydrolysable bond is one that is labile and subject to being broken under hydrolysis conditions employed to produce the solid silica network in the presence of water as a reactant, and a suitable catalyst if appropriate, so that the atoms linked by the hydrolysable bond become dissociated from one another. The moieties linked to the silicon (or other metallic or nonmetallic) atom via hydrolysable (labile) bonds are referred to as leaving groups, because following hydrolysis (or whatever the particular sol gel reaction used) they will be dissociated from (they will 'leave') the silicon or other metallic or semimetallic atom, and consequently will not be part of the resulting network.

To incorporate non-native (non-hydroxyl) functional groups to support polymer cross-linking as further described below, a functionalized silica precursor species is included in the hydrolysis reaction. To incorporate flexible linkages or 'flex links' into the ceramic oxide network, a flexible linking precursor of the form $(R)_y(R^1)_x$-M-L-M-$(R^1)_{x'}(R)_{y'}$ is incorporated into the network-synthesis reaction as mentioned above, wherein R, $R^1$, x, x', y, y' M and L are all defined as above. The flexible linkage, L, is selected to provide a desired degree of flexibility to the resulting solid gel network and can take any suitable form. Throughout the remainder of this description, for brevity the case will be assumed where x and x' are both zero, meaning that only leaving groups, Rs, are attached to the M atoms in the flexible-linkage precursor. It will, of course, be appreciated that retained groups, $R^1$s, can be incorporated into any of the following methods to achieve desirable results, i.e. the incorporation of $R^1$ groups into the finished ceramic-oxide network in a concentration that is function of the concentration of flexible-linkages also incorporated.

In one embodiment, L can be a straight-chain hydrocarbon linkage (branched or unbranched), in which case the flex link precursor would have the form

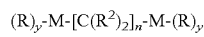

wherein:
M, R and y are as described above;

$R^2$ can be H or any substituted or unsubstituted alkyl, aryl or other group that will not impermissibly interfere with the reaction(s) that is or will be used to produce the ceramic oxide particle network from the ceramic oxide precursors (functionalized or unfunctionalized), and wherein each $R^2$ can be the same as or different from other Rs or $R^2$s; and n is a positive integer, preferably not more than 50, preferably not more than 40, preferably not more than 25, and most preferably is in the range of 6-20 or 6-25.

The value of n in the above formula is most preferably 6-25 as mentioned above. Shorter oligomers such as $(RO)_3Si(R^2)_{2-4}Si(OR)_3$ wherein M is selected to be silicon, are known to produce ring structures that can prevent gelation. Conversely, strands longer than n=25 may interfere with gelation through steric hindrance and/or by keeping the silica particles in solution.

To achieve maximum flexibility, it may be desirable that all $R^2$s in the above formula are hydrogens instead of branched side-chains or other moieties that may introduce steric or other hindrances to the flexing of the C-chain backbone of the flexible linkage. In an alternative to the embodiment shown above, the straight-chain hydrocarbon flexible linkage may include one or a number of unsaturated bonds so long as the overall flexible linkage remains sufficiently flexible. However, it is desirable to avoid unsaturated bonds in the flexible linkage to provide maximum flexibility, particularly for flexible linkages having a chain length, n, below 25 and more particularly for values of n equal to or lower than 10 or 6.

The flex link precursor is incorporated into the reaction mixture together with the alkoxysilane used to produce the ceramic oxide network. Specifically, in the case of a silica network that is to use a straight-chain flexible linkage to provide flexibility, the reaction mixture can include an alkoxysilane such as TMOS or TEOS and a flex-link precursor that can be in the form of a bi-siloxyl-terminal flex link precursor having the following form:

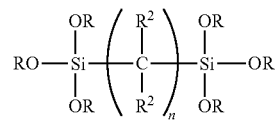

wherein R, $R^2$ and n are defined as above and Si, O and C each represent the respective atoms. The above structure assumes no retained ($R^1$) groups are attached to the Si atoms. Of course, such groups also can be provided, for example as reactive sites to anchor polymer-based cross-linking as described further below. In the embodiment now being discussed, no such retained groups are included in the flexible-linkage precursor.

The alkoxysilane and bi-siloxyl-terminal flex link precursor are combined and reacted with water under appropriate hydrolysis conditions to copolymerize them and produce a gelled network of silica particles comprising silicon atoms from the alkoxysilanes and the flex link precursor. Specifically, as the hydrolysis and condensation reactions proceed a silica network is formed consisting of silicon atoms from the alkoxysilane and the bi-siloxyl-terminal flex link precursor molecules that were originally present, wherein adjacent silicons are joined to one another via a —O— linkage to produce a solid network having the nominal empirical formula $SiO_2$ as mentioned above. Because the —$[CR^2_2]_n$— linkage is stable (non-labile) under hydrolysis conditions, only the three —OR groups (with reaction-labile Si—O bonds) are removed from the bi-siloxyl-terminal flex link precursor during the synthesis reactions. Consequently, the Si atoms in that precursor remain linked to one another via the flexible —[CR$^2{}_2$]$_n$— linkage and are integrated into the network via Si—O—Si bonds at their three other valences.

Figure 4:
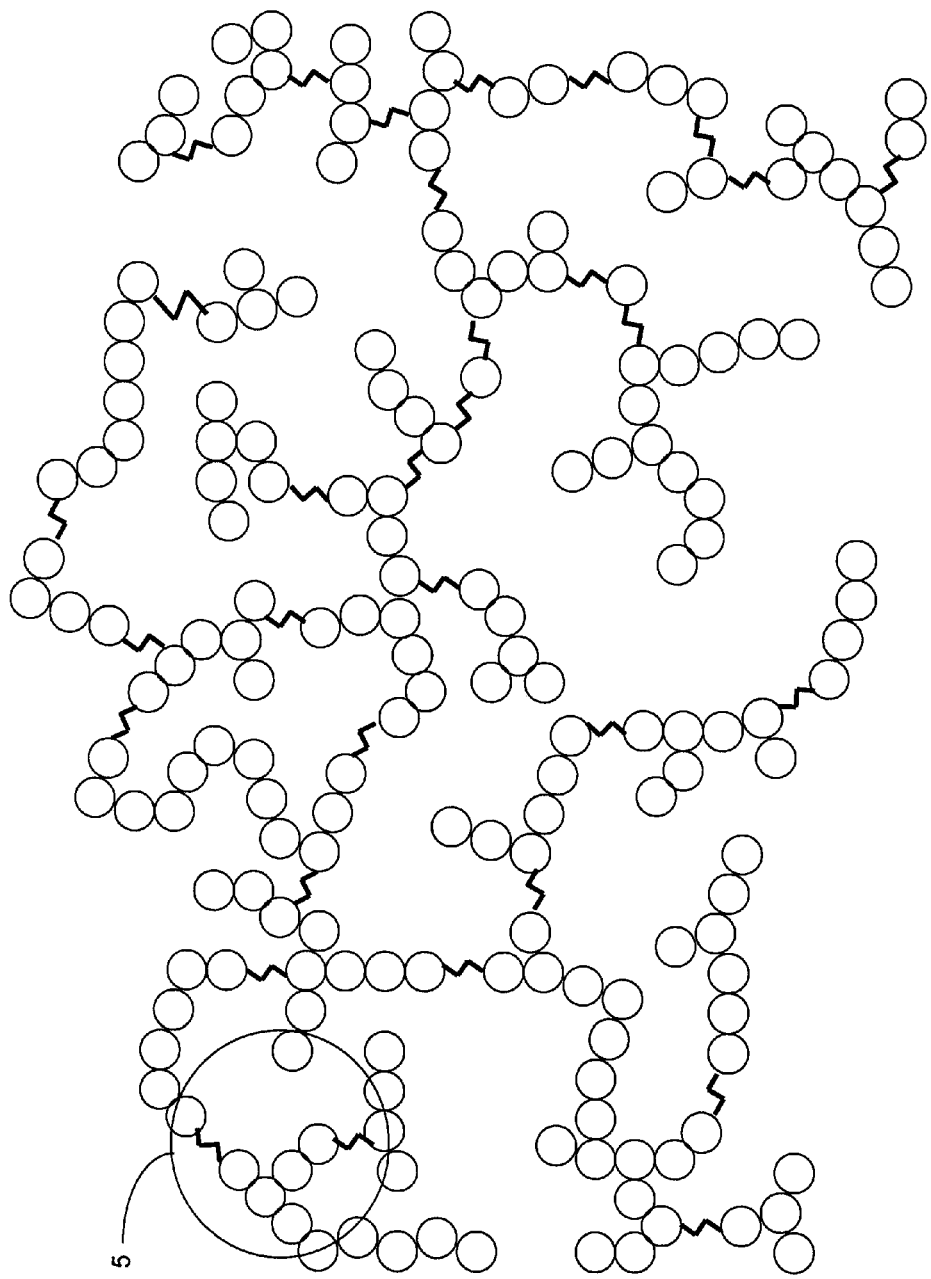
FIG. 4 is a schematic illustration of the solid silica network of FIG. 2, but incorporating flexible linkages as disclosed herein periodically dispersed throughout the network between adjacent secondary particles.

As mentioned previously, the resulting solid silica network (still a 'wet' gel because it is not yet dried of the reaction solvent) consists of secondary particles, each made of smaller and fully-dense primary particles, arranged in pearl-necklace configuration, with secondary-particle strands interlocking in three dimensions. The space defined between interlocking secondary-particle strands defines a mesoporosity of the network as illustrated in FIGS. 2 and 4, which contributes to volume void fractions of at least 80, preferably 85, more preferably 90, most preferably 95, percent, or higher as also mentioned above. In addition to the pearl-necklace strands, a silica gel prepared as above is believed to incorporate a plurality of flexible linkages consisting of the 'L' portion of the flex link precursors above (shown in FIG. 4, wherein the ⌇⌇ segments correspond to the 'L' portion mentioned above). In the case of a silica gel made using the straight-chain flex link precursor shown above, those linkages will have the structural formula —Si—[C(R$^1$)$_2$]$_n$—Si—. It is believed the flexible linkages are primarily interposed between adjacent secondary particles periodically throughout the silica network as shown in FIG. 4, wherein they have the effect to break up the otherwise long pearl-necklace-configured chains of secondary silica particles, which are believed to be relatively rigid and inflexible.

It is believed that incorporation of large, sterically hindered species (such as the flexible linkages described herein) at the surfaces of the secondary particles of a ceramic oxide network is thermodynamically favored for a number of reasons compared to intra-particle incorporation. Without wishing to be bound by theory, the following is noted. First, the primary particles that make up secondary particles are fully dense, having substantially no porosity. Relatively bulky species such as the L groups mentioned above would be strongly sterically disfavored compared to the much more compact oxygen linkage (—O—) within and between the fully dense primary particles that make up secondary particles. In addition, the flex link precursor-source silicon atoms, having the non-hydrolysable bond to the L group, each have one less bonding site compared to the fully hydrolyzed silicon atoms from tetra-alkoxysilanes, which may tend to terminate network growth or linkage. If these silicon atoms were concentrated internally, they might be expected to disrupt gellation and the formation of a uniformly dense and fully expansive solid silica network. Such constraints are not present at the surfaces of the secondary particles. The secondary particle surfaces define a vast network of relatively large mesopores that can easily accommodate the steric bulk (compared to compact Si atoms) of flexible L groups concentrated at and extending from those surfaces. Furthermore, because the secondary particles are linked to one another only in relatively narrow neck regions to form the above-mentioned pearl necklace structure, silica network propagation above the secondary particle surfaces for the most part does not occur, and there is less need for a fourth Si-bonding site. For all these reasons the incorporation of the flexible linkages at and between adjacent secondary-particle surfaces within the silica network may be thermodynamically favored compared to intra-particle integration.

The observed behavior of wet gels and their corresponding aerogels prepared with flexible linkages also supports the conclusion that those linkages are incorporated between secondary-particle surfaces as illustrated in FIG. 4. Specifically, as seen in Example 3 below, wet gels have been produced that are highly flexible in that they can be bent into various configurations without breaking or fracture. As also seen below, wet gels can be dried to produce dry aerogels through simple air drying, without the need for supercritical CO$_2$-mediated drying or multiple solvent exchange steps, with no or negligible shrinkage and no perceptible fracture. These observed behaviors are explained by our theory that the flexible linkages described herein are incorporated primarily in between adjacent secondary particles dispersed throughout the network as shown in FIG. 4, thereby segmenting those strands. The incorporation of such flexible linkages, it is believed, has the dual effects of shortening the relatively rigid secondary-particle strands (by segmenting them) and enabling the resulting shorter strands to bend or flex relative to one another via the flexible linkages between them.

In addition to the straight-chain flexible linkages described above, the linkage, L, may also incorporate intermediate atoms other than C, for example nitrogen, so long as none of the bonds in that linkage are susceptible to hydrolysis under the network-synthesis conditions. In that case, the degree of polymerization, n, from above preferably corresponds to the total number of atoms in the chain, including C and non-C atoms. Several examples of flex link precursors that may be suitable to produce flexible linkages in a silica aerogel are listed below, which list is provided by way of example only and not limitation:

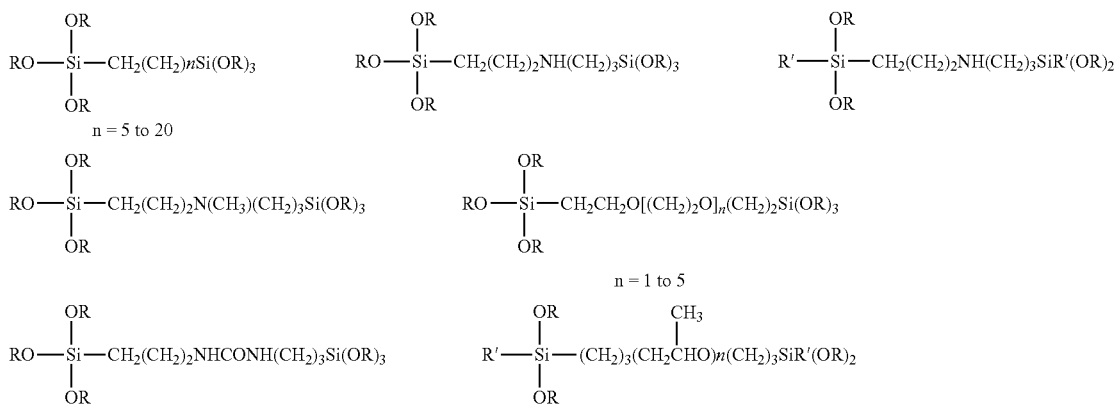

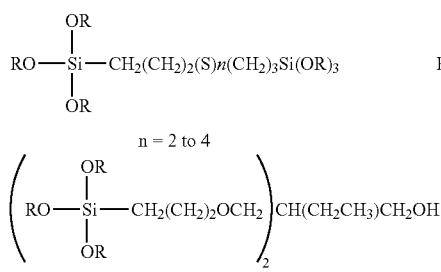
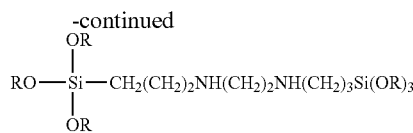

wherein Rs in each of the above can be individually selected as hydrogen, alkyl or other moieties but preferably are selected to be the same as one another in the same molecule, and R's above preferably are different from Rs attached to the same atom therewith.

In addition, the flexible linkage may also incorporate intermediate aromatic functionality or unsaturated side chains, for example:

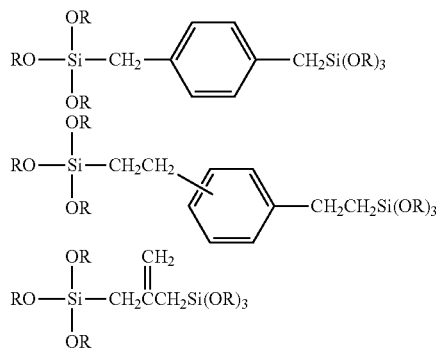

The flexible linkage portion, L, of the flex link precursor, and correspondingly the flexible linkage integrated into the silica network, may optionally include reactive side chains or other moieties to support a further cross-linking reaction. Specifically, as described in detail below it may be desirable to polymer cross-link the ceramic oxide network, and reactive moieties compatible with the polymer cross-linking chemistry that is used may be incorporated into the flexible linkages; provided that such moieties do not interfere with the network-synthesis reactions. Still further, the flexible linkages may also be provided or designed to impart additional desirable characteristics to the resulting flexibility-improved aerogel, such as groups that promote or increase fire retardance, polarity or charge-carrying characteristics or other desirable properties.

By interposing the flex links into the secondary-particle strands, thereby reducing the effective length of the rigid particle-to-particle strands and providing flexible linkages in between them, the observed flexibility of the aerogels is increased. As will become evident below, the incorporation of flex-links into certain compositions of silica aerogel has been effective to eliminate the need for supercritical $CO_2$-mediated drying, with no apparent shrinkage or pore-structure collapse between the wet and dried-aerogel states. Without wishing to be bound by theory, it is believed that the flex links incorporated periodically throughout the ceramic network of interlocked strands of secondary particles increase the flexibility of the backbone network, thus permitting it to adapt more easily and to accommodate oppositely- or differently-acting forces that result from surface-tension effects as the solvent evaporates from the pore network. Specifically, by shortening the effective length of those strands, and introducing a flexible linkage in between the shorter strands, the whole network is believed to be made more flexible or malleable, and capable to adapt and flex in response to counteracting forces that otherwise may have caused brittle failure of a rigidly-constrained network. In other words, the rigid network is made more flexible by shortening its rigid members (the pearl necklace strands of secondary particles), and by introducing a flexible linkage periodically between adjacent ones of those strands.

Several examples of particular flex-link species have been discussed above. However, it will be evident that the selection or design of a particular flex-link species can be undertaken in each specific case to achieve an appropriate or desirable degree of flexibility as well as other physical characteristics. Such selection and/or design will be a matter of routine based on the present disclosure. For example, the degree of flexibility of the flexible linkages will depend on, among other things, the, length of that linkage, whether it is a straight-chain or branched, as well as other recognizable factors such as the prevalence of rotatable bonds. Much rotation is possible for carbon-carbon or carbon-heteroatom single bonds in a polymer chain. Alternatively, higher order (double or triple) carbon-carbon bonds as well as aromatic rings in the flexible linkages will restrict rotation, and may inhibit flexibility. Flexible linkages incorporating a high degree of these groups and/or unsaturated bonds may be expected to produce a lower degree of flexibility in the resulting aerogel for a given amount of the flex-link precursor introduced in the synthesis reaction.

Conversely, flex links having numerous ether linkages, which permit a high degree of rotation, will be substantially more flexible. The resulting flexibility of the overall aerogel may depend on the proportion of ether linkages in the flex links. At this point, it should be evident that a person having ordinary skill in the art will be able to design a wide variety of flexible-linkage architectures, based on a variety of structures, additive functional groups, other structural linkages and moieties to produce aerogels having characteristics suitable to any number of potentially desirable applications. Whether the flex-links include side groups or moieties capable to be cross-linked via the polymer cross-linking architecture described below is also a factor that will impact the overall degree of flexibility of the resulting aerogels.

Some amount of routine experimentation may be required to optimize or balance the contributions of competing effects of various moieties and/or side groups present in the flex links. But such experimentation will be within the capability of a person having ordinary skill in this art. In addition, numerous (e.g. two or more) different flex-link species (and corresponding flex-link precursors) may be used having differing structure; i.e. one may have few or no rotatable bonds and/or a shorter chain length compared to the other, and their ratio tuned to achieve a desired degree of flexibility. Of course, the total range of available flexibility may be constrained within broad limits based. The Examples below demonstrate that a large degree of adjustment is possible by varying at least the concentrations of the silane species (including functionalized, unfunctionalized and flex-link precursor species) that go into gel synthesis. A degree of adjustment should also be possible by varying factors such as those described above.

As already mentioned, in addition to improving flexibility it may also be desirable to polymer cross-link the secondary-particle pearl necklace strands in the aerogel to impart greater strength. Methods of providing such a cross-linking architecture to improve aerogel strength will now be described.

To provide such a polymeric cross-linking structure, methods described in publication US 2004/0132846 can be used, which rely on providing polyurethane linkages between native OH groups at the surfaces of secondary silica particles. However, it may be desirable to incorporate different, non-native (non-OH) functionality at those secondary particle surfaces to anchor the polymer cross-linking architecture, and/or to accommodate other cross-linking chemistries other than polyurethane, that would not necessarily be compatible with (able to link to) surface-bound OH groups.

To incorporate such non-native functional groups into the secondary-particle surfaces, a functionalized ceramic oxide precursor can be incorporated into the reaction mixture for forming the gel network as mentioned above. Like the alkoxysilane species also described above, which contains a silicon atom bonded to other species via only hydrolysable bonds, a functionalized silica precursor species includes a silicon atom bound to at least one, preferably to at least two, most preferably to three, other moieties via a hydrolysable bond (i.e. a bond that is labile under the particular reaction conditions), so the silicon atom can be integrated into the silica network during the hydrolysis reaction, e.g. with TMOS or TEOS. In addition to the leaving group(s) attached to the silicon atom, the functionalized silica precursor species also has at least one non-hydroxyl functional group attached to the Si atom via a non-hydrolysable (i.e. non-labile) bond. A non-hydrolysable bond is one that is not subject to being broken under the hydrolysis conditions noted above.

In an exemplary embodiment, it is desirable to incorporate amine functionality bound to the secondary-particle surfaces. In that case, a functionalized silica precursor such as 3-aminopropyl triethoxysilane or 'APTES' may be incorporated into the reaction mixture for making the silica aerogel. Similar to TMOS, which has four alkoxy moieties, APTES has three alkoxy moieties (ethoxy groups) linked to the central silicon atom via a hydrolysable bond. However, unlike TMOS, APTES also includes a fourth moiety that is a 3-aminopropyl group linked to the silicon atom via a non-hydrolysable Si—C bond. Under hydrolysis conditions, the three alkoxy bonds in APTES are broken and the associated ethoxy groups converted to ethanol. This frees three bonding sites on the silicon atom that now can be linked to oxygen atoms in the silica network, while the latter, fourth bond is not broken during hydrolysis. Consequently, the APTES-source silicon atom will continue to carry the 3-aminopropyl moiety with the terminal —$NH_2$ functional group after it is integrated in the silica network. In the case of silica formed from copolymerizing an alkoxysilane and APTES, it has also been found the resulting solid network exhibits the same basic hierarchical structure described above, having nanoporous secondary particles (particle size ~5-10 nm), composed of agglomerations of smaller and highly dense primary particles (particle size ~<2 nm), linked in long interconnected strands to produce an interconnected pearl necklace structure. It has been found that a large portion of the aminopropyl-linked silicons are located at the surfaces of the secondary particles, with the aminopropyl groups decorated over the secondary particle surfaces and extending into the superjacent void space (mesopores). It is noted that when APTES is used to provide amine functionality, it is unnecessary to incorporate a separate catalyst into the hydrolysis reaction because the amino groups on APTES provide more than adequate basic character to the sol to catalyze the hydrolysis reaction. In fact, it has been necessary in experiments to cool the TMOS/APTES solution/water mixture to slow the gellation rate and permit pouring of the sol into a desired mold prior to substantial gellation. In the case where it is desired to incorporate both surface-bound amine groups into the secondary particles as well as increased flexibility to the resulting silica aerogel, TMOS, APTES and the bi-siloxyl-terminal flexible linkage precursor all can be combined into the sol reaction mixture under hydrolysis conditions to produce the silica gel. The resulting gel structure is shown schematically in FIG. 5, wherein flexible linkages are illustrated periodically between adjacent secondary silica particles, and amine groups are shown decorated over the secondary-particle surfaces. The flexible linkages impart greater flexibility to the silica gel network as described previously, whereas the amine groups provide anchors for further polymer cross-linking structure to provide a conformal polymeric coating over the secondary-particle network as explained below.

It is believed, and experimental results have suggested, that integration of the APTES-source silicon atoms at the secondary particle surfaces is favored compared to intra-particle integration within the silica network. Potential explanations for the apparent preference of the aminopropyl-linked silicon atoms to be incorporated at secondary particle surfaces are similar to the reasons it is believed that the flexible linkages are incorporated primarily between secondary-particle surfaces and not within those particles. Specifically, the primary particles are fully dense with substantially no porosity, and the relatively bulky aminopropyl group ($NH_2$—$CH_2$—$CH_2$—$CH_2$—) would be strongly sterically disfavored compared to the much more compact oxygen linkage (—O—) within the fully dense primary particles. Thus, the APTES-source silicon atoms, having the non-hydrolysable aminopropyl group and therefore one less bonding site compared to the fully hydrolyzed silicon atoms from alkoxysilane, may tend to terminate network growth or linkage. If these silicon atoms were concentrated internally, they might be expected to disrupt gellation and the formation of a uniformly dense and fully expansive solid silica network. Furthermore, experimental evidence suggests that APTES itself does not gel. Hence both steric considerations and the lack of a fourth bonding site compared to the alkoxysilane-source silicon atoms suggest the APTES-source silicons would be relatively disfavored internally, within either the primary or the secondary silica particles. However, such constraints are not present at the surfaces of the secondary particles for reasons already explained. In addition to the above, hydrolysis of the alkoxy groups of APTES is slower than that of TMOS. Therefore, the incorporation of the APTES-source silicon atoms at the surfaces of secondary particles within the silica network may be thermodynamically favored compared to intra-particle integration of these silicons.

Figure 5:
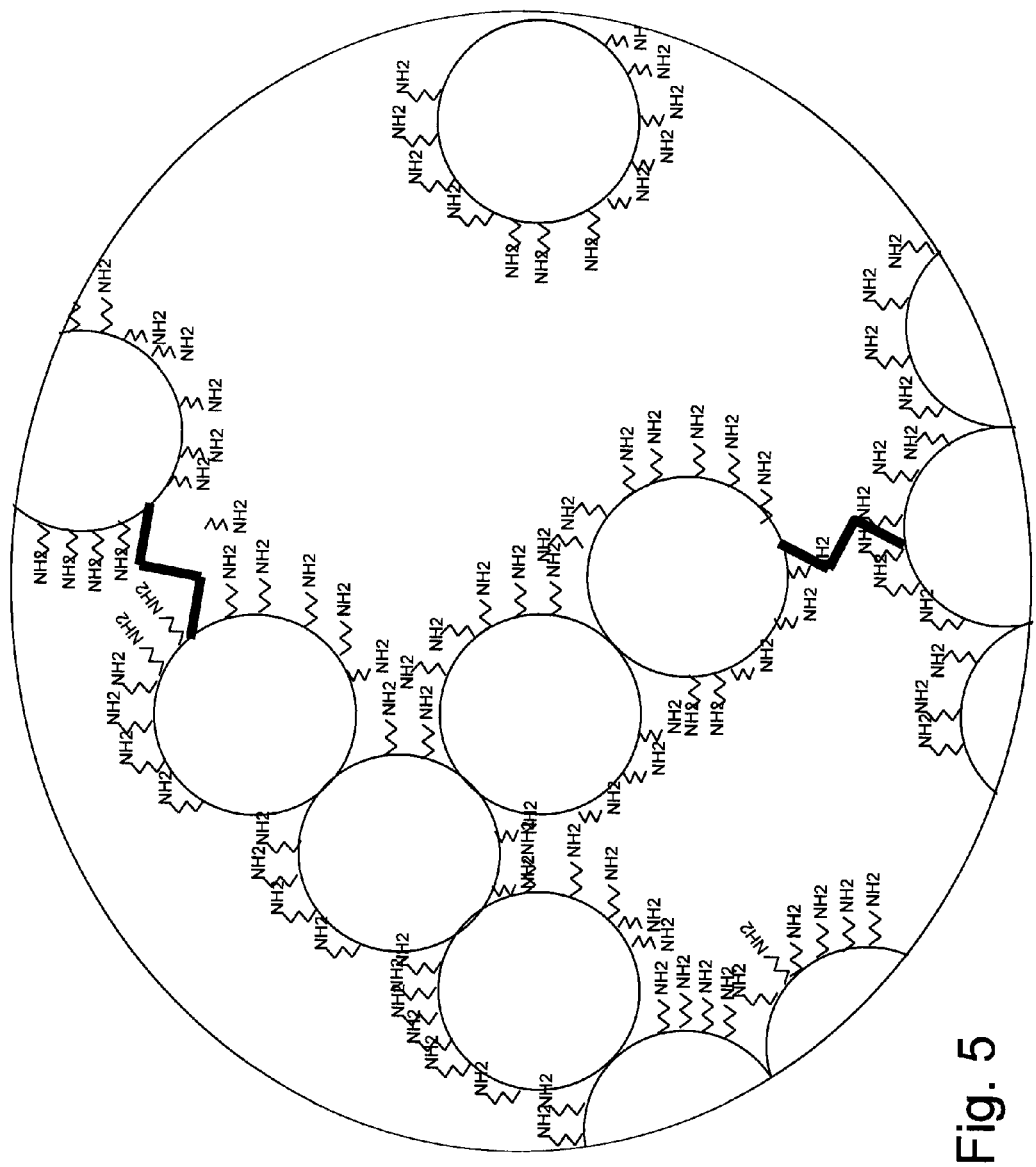
FIG. 5 is a close-up schematic illustration of the structure of the solid silica network taken at circle "5" in FIG. 4, showing interconnected strands of secondary particles having flexible linkages periodically dispersed therein between adjacent secondary particles, as well as non-native aminopropyl functionality incorporated at the surfaces of the secondary silica particles, for example by incorporation of APTES into the gel-synthesis reaction.

Following hydrolysis of TMOS, APTES and the bi-siloxyl-terminal flex link precursor species as described above, the resulting wet gel framework comprises a solid silica network having a structure illustrated schematically in FIG. 5 as noted above, wherein the ⋁⋀ linkages will have the form —Si-L-Si—. Adjacent secondary particles in the secondary-particle strands are connected either directly to one another via —Si—O—Si— linkages between the surfaces of adjacent particles at relatively narrow neck regions (FIG. 3), or otherwise via flex links as illustrated in FIGS. 4-5. As noted previously, the flex links consist of the portion, L, of the flex link precursor species that is left once all hydrolysable bonds have been severed, leaving the terminal silicons free to interact and copolymerize during the hydrolysis/condensation reactions that propagate and form the silica network.

In FIG. 5, flex links are provided between adjacent secondary particles in conjunction with the incorporation of aminopropyl functional groups decorated over the surfaces of secondary particles. Of course, terminal hydroxyl groups also will be present on the surfaces of the secondary particles, however these are not illustrated. The surface-bound aminopropyl groups (or other non-native functional groups if so-incorporated) can be further reacted with a polymer or a polymerizable species, or other species that can serve as a base for linking or forming a polymer chain to the secondary particle surfaces as part of a polymer cross-linking structure between secondary particle strands in the solid silica network. Hence, while the flex links impart a degree of increased flexibility to the resulting aerogel, a polymer cross-linking structure (in the form of a conformal coating) can be used either to provide additional physical strength to the aerogel or enhance the flexibility depending on the nature of polymer (an elastic polymer structure, for example). It may even be possible to enhance both strength and flexibility. It is reiterated that while the solid silica network itself may be considered a 'polymer' produced from the copolymerization of TMOS, APTES (or other functionalized silica precursor) and the flex link precursor species, the term 'polymer' is reserved herein to refer to different, preferably organic, polymeric species or chains, non-native to a ceramic oxide network, that link or which are provided to cross-link that ceramic oxide network. The term 'cross-link' and cognate terms such as 'cross-linked,' 'cross-linking' and the like herein refer to linkages composed of polymeric structures non-native to the ceramic oxide network that extend between or link, or which are provided to link, different portions or points within that ceramic oxide network, either from native OH groups at the surfaces of secondary aerogel particles or from other, non-native functional groups provided at those surfaces, such as amine (e.g. aminopropyl) groups.

Whether or not it includes non-native functional groups at the secondary-particle surfaces (through incorporation of functionalized silica precursor species into the reaction mixture), the gel that is produced following the synthesis (hydrolysis and condensation) reactions is initially in the form of a sol gel or 'wet' gel whose porous structure is filled with the hydrolysis solvent, hydrolysis reaction byproducts (such as MeOH from TMOS, EtOH from the ethoxy groups of APTES as well as from TEOS if used, etc.) and other unconsumed species. If desired, at this point the wet gel can be cross-linked using a suitable polymer species or precursor (such as an appropriate monomer) to produce a conformal polymer cross-linked coating as referred to above. For example, the functional (amino) groups on the surfaces of the secondary particles can be reacted with an appropriate monomer or other species for forming or linking to a compatible polymer chain. Several different embodiments for providing such a conformal polymer cross-linked coating are described below.

In one embodiment a diisocyanate can be linked to the terminal amino groups on the surfaces of the secondary particles via a urea linkage according to equation (1) if the gel has been functionalized with amino groups.

(1)

The resulting terminal isocyanate group, now attached to the secondary particle surface via the urea linkage, can be reacted (polymerized) with additional polyisocyanate groups to produce a polyurea polymer structure, e.g. as in Eq. 2.

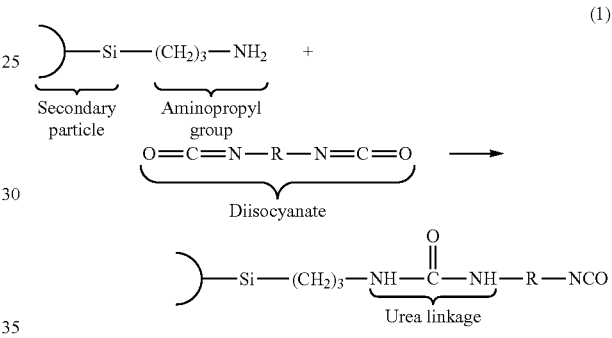

(2)

To drive this polymerization reaction water adsorbed on the silica surfaces is sufficient. The terminal isocyanate group in the product of Eq. 2 above likewise can be reacted with an amino group at the surface of the same or a different secondary particle to produce a polyurea linkage or 'cross-link' between two different secondary particles, for example between adjacent secondary particles in the neck region between them, or between different sites on the same secondary particle, Eq. 3.

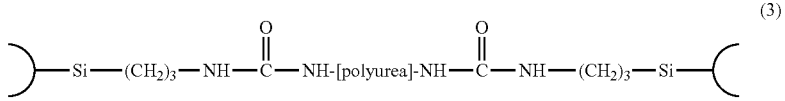

(3)

Alternatively, the above polymerization (cross-linking) reactions can be carried out with an isocyanate that is greater than 2-functional (i.e. having more than two functional NCO groups). For example, 3- and 4-functional isocyanates also can be used. It will be understood that just as in conventional polyurethane chemistry where isocyanates are prevalent, the greater the isocyanate functionality the more highly branched the resulting cross-linking polymeric structure will be, and consequently the more rigid and inflexible the resulting cross-linked ceramic oxide (silica) network may become. However, in applications where flexibility is of little concern, highly branched cross-linking structures may be desired to impart greater strength to the ultimate silica aerogel product (produced after the cross-linked sol gel is dried). This added strength will come at a cost in terms of a small increase in weight, however, because a more highly cross-linked aerogel will be more dense compared to uncross-linked aerogel. Alternatively, the degree of branching, regulated by isocyanate concentration, may be controlled in conjunction with the degree of introduced flexibility, regulated by the concentration of flex-link precursor in the network-synthesis reaction, to achieve an appropriate balance of the two effects and produce an aerogel having tunable or application-specific physical properties. Co-reactants can also be used with the 2- 3- or 4-functional isocyanates to enhance flexibility. For example, OH-terminated glycols or amine-terminated ethylene oxides will co-react with the isocyanates to produce more flexible polymer cross-links.

In all of the above alternatives, polyurea chains that make up the polymer cross-linking may be linked together via branched polyurea chains, with the degree of branched linkages between the polymer chains depending in part on whether a 2-, 3- or 4-functional isocyanate is used for polymerization. Alternatively, mixtures of polyfunctional (2-, 3- and/or 4-functional) isocyanates also can be used. It will be further recognized there is the potential for additional cross-linking involving further reaction of secondary amine (—NH—) groups in polyurea to form tertiary amines (—N<) (allephanates and biurets, respectively), as is common to all polyurethanes. Still further, if appropriate side groups are provided on the flexible linkages as mentioned above, then the polyisocyanate or other cross-linking structure may be linked directly to the flexible linkages as well.

In the immediately foregoing reactions, 'R' can be any group or moiety to which one or multiple —N═C═O groups can be attached, as the individual case may be. For example, 'R' can be or include a straight or branched alkyl or aryl group, aromatic group, olefinic group, or any combination of this, with or without additional functional species, so long as such additional functional species will not intolerably interfere with the formation of urea linkages between isocyanate groups on different monomers, or between an isocyanate group and a surface-bound amine group in the ceramic oxide network. It is contemplated that 'R' can be provided or designed to impart additional desirable characteristics to the resulting polymer cross-linked ceramic oxide aerogel, for example incorporating additive functional groups as described more fully below.

As a further example, a polyepoxide also can be linked to a terminal amino groups on the surfaces of a secondary particles via an epoxy linkage as shown in Eq. (4).

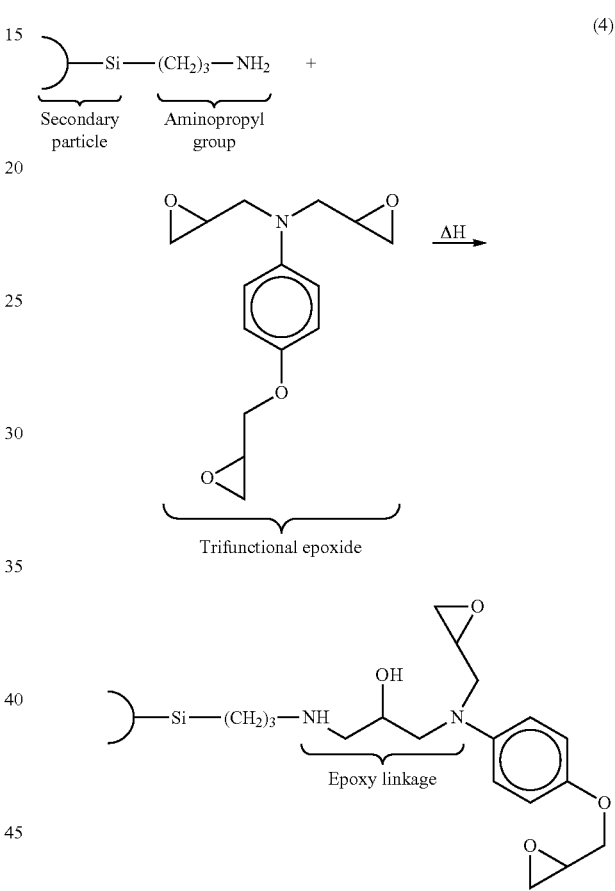

In Eq. 4, a trifunctional epoxide (N,N'-diglycidyl-4-glycidyloxyaniline) is reacted with the terminal amino group at the surface of the secondary particle. This results in a difunctional epoxide moiety attached to a secondary particle surface. Each of the epoxide groups of this difunctional epoxide moiety in the product of Eq. 4 can react (polymerize) with a) a yet-unreacted terminal amino group at the surface of the same or a different secondary particle, the latter resulting in inter-particle cross-linking, or b) at temperatures above 150° C., other epoxide groups attached to the surface of the same or a different secondary particle. An exemplary mechanism involving the difunctional epoxide product in Eq. 4 bound to each of two secondary particles, and a third secondary particle having an as-yet unreacted surface-bound amino group, is illustrated in Eq. 5.

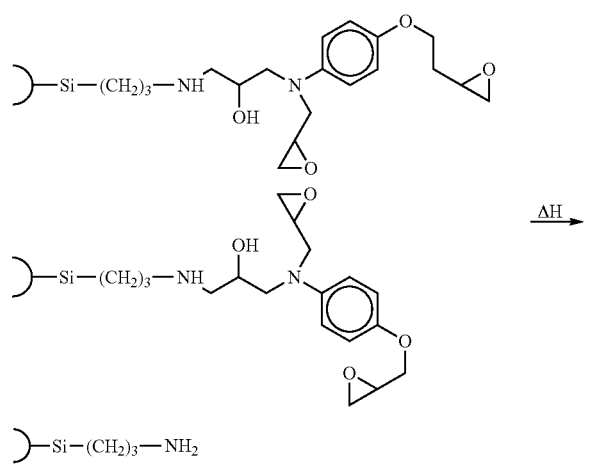

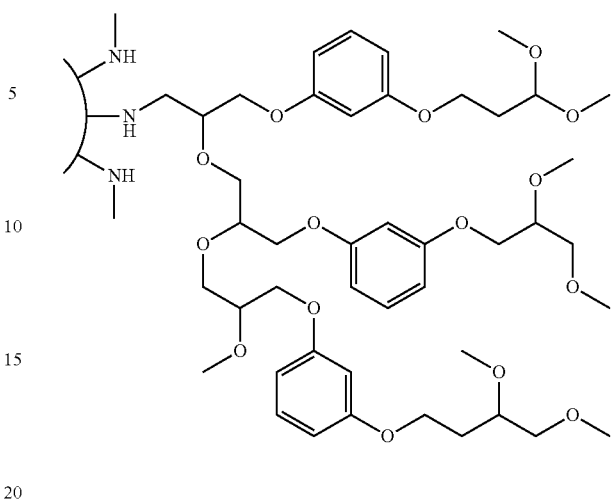

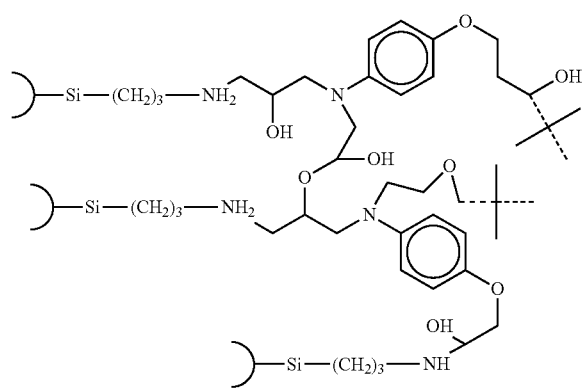

It will be understood that the exemplary mechanism shown in Eq. 5 is merely illustrative of numerous combinations of epoxide-epoxide and epoxide-amine reactions that are possible to produce a three dimensional polymeric epoxy network structure. In addition, it will be understood that di-, tetra-, or other polyfunctional epoxides also can be used, or combinations of them with each other or with tri-functional epoxides such as the one described above. For example, the following polymer network architecture using 1,3-diglycidyloxybenzene as a difunctional epoxide monomer, Eq. 6, also is within the scope of the invention:

A cross-linked epoxy polymeric network is produced via epoxy linkages between epoxide groups on different polyepoxide monomers (at temperatures above 150° C.), as well as between such groups and surface-bound terminal amino groups within the ceramic oxide particle network. (Epoxies also will react with SiOH surface groups, although to a much lesser extent.) The result is an epoxy cross-linked solid ceramic oxide (silica) network, in the form of a wet gel whose pore structure is saturated with the solvent used to carry out the epoxy polymerization reactions. Analogous with the polyisocyanate network discussed above, an epoxy polymeric network will provide epoxy linkages or 'cross-links' between different secondary particles, for example between adjacent secondary particles in the neck region between them, or between different sites on the same secondary particle. At elevated temperatures or in the presence of catalyst, branched epoxy linkages between epoxy polymer chains are also possible. Under conditions that have been employed to produce the epoxy cross-linked silica networks described here (no catalyst and relatively low temperatures), epoxides do not typically form large networks or chains of epoxy oligomer (monomer). Hence, under these conditions the resulting epoxy cross-linked silica network is primarily an epoxy monolayer over the surface of the secondary particle strands (pearl necklaces).

The foregoing discussion has been provided with respect to several specific di- and tri-functional polyepoxides. However, it will be understood that other polyfunctional epoxides having the general form:

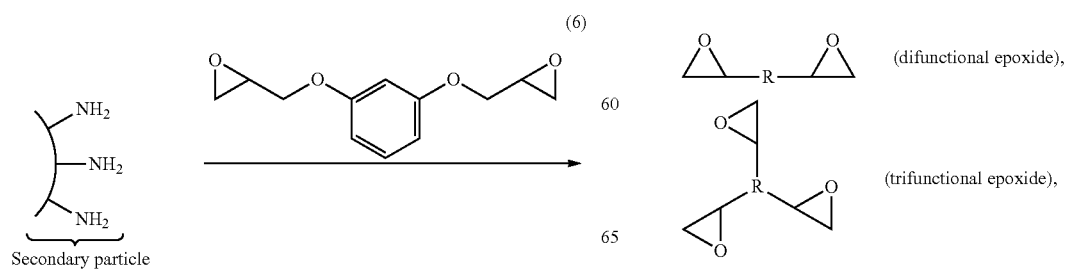

(6)

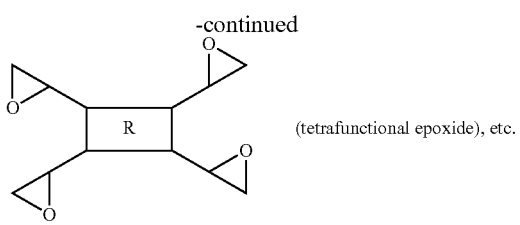

(tetrafunctional epoxide), etc.

also could be used, where 'R' is or can be or include any structure compatible with the epoxy cross-linking chemistry, similarly as described above.

In still a further example of another polymeric cross-linking architecture, a styrene-containing species also can be linked to the terminal amino groups on the surfaces of the secondary particles via an appropriate linkage. The attached styrene group then can be reacted (polymerized) with other styrene-containing monomers to produce a polystyrene cross-linked polymeric network. For example, Eq. (7) below illustrates a reaction for attaching a styrene group to a surface-bound terminal amino group attached to a secondary particle of the ceramic oxide network.

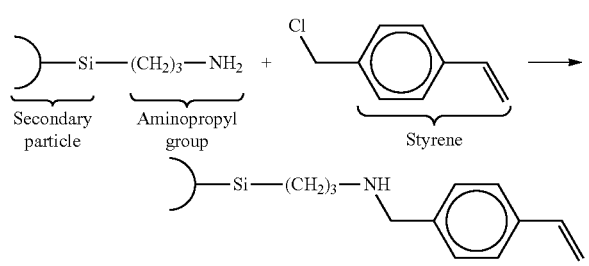

(7)

In Eq. 7, the styrene-containing species used to attach the styrene group to the terminal amine is 4-vinylbenzyl chloride, which contains a styrene moiety as shown in Eq. 7. This species is convenient because the terminal chloride reacts readily with the amine to link the amine and the residual p-methylstyrene moiety, producing HCl as a byproduct. In addition, other suitable styrene-containing species, having other functional groups that will react with the amino group to attach the styrene group to the ceramic oxide, can be used, (styrene functionalized epoxides, etc.). However, the preferred method is to co-polymerize p-trimethoxysilyl-styrene or vinyltrimethoxysilane (VTMS) (as the functionalized silica precursor) with TMOS, analogously to the copolymerization of APTES (though amine catalyst is necessary) to apply the styrene moiety directly to the surface of the nanoparticles.

Once styrene groups have been bound to internal surfaces of the solid ceramic oxide network, they can be reacted (polymerized) with other styrene monomers to produce a polystyrene cross-linked polymer network, for example as illustrated in Eq. 8. The styrene functionalized gels are placed into solutions containing the monomers of choice and AIBN as the initiator, and the polymerization occurs at elevated temperatures such as 75° C., or 75° C. to 100° C.

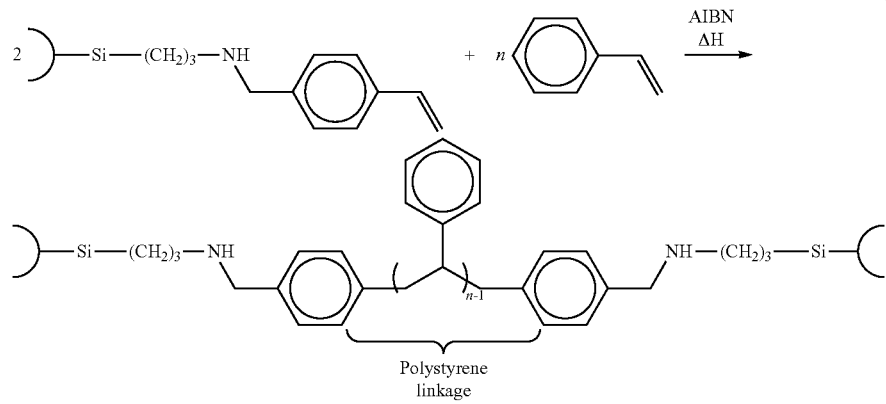

(8)

It will be understood that Eq. 8 is merely illustrative of a possible polystyrene cross-linking mechanism using native, non-functionalized styrene monomer to provide the polymeric cross-links. The actual cross-linked polystyrene network produced through polymerization of styrene monomers will include polystyrene chains of varying length depending on the concentration of additional monomer, extending between amino groups at the surfaces of different secondary particles, as well as between such groups attached to the surface of the same secondary particle. As with the previously described cross-linking species, polystyrene chains also may be provided between two adjacent secondary particles linked at a neck region in the same strand, as well as between different secondary particles in the same or in different strands. Also, alternatively to non-functionalized styrene monomer, other functionalized styrene-containing monomeric species (e.g. of the form R-[styrene], or R-[styrene]$_n$ also could be used. Similarly as before, 'R' can be or include any structure compatible with styrene polymerization to produce a polystyrene cross-linking architecture. Examples of styrene-containing monomeric species that have been successfully used to produce polystyrene cross-linked silica aerogels are 4-vinylbenzyl chloride and pentafluorostyrene, as well as mixtures thereof. It will be understood that to produce a branched polystyrene network, it may be necessary or desirable to incorporate at least some functionalized styrene-containing monomers, or otherwise monomers containing at least two styrene groups. Otherwise, pure, non-functionalized styrene may produce primarily straight and unbranched polystyrene chains as known in the art.

Also, generally it is desirable to utilize a radical initiator species to induce styrene polymerization. In the mechanism illustrated in Eq. 8, azobisisobutyronitrile (AIBN) is employed as a radical initiator. However, other suitable radical initiators can be employed, e.g. peroxy-based initiators including benzoyl peroxide can also be utilized under similar thermal conditions to obtain the polymerization.

As a further example, a polyamic acid also can be linked to terminal amino groups on the surfaces of the secondary particles via an anhydride linkage as shown in Eq. (9).

In Eq. 9, a polyamic acid terminated with anhydride is reacted with terminal amino groups at the surface of the secondary particles. This results in amic acid moieties attached to secondary particle surfaces. Each of the anhydride groups shown in Eq. 9 can be reacted (polymerized) with a yet-unreacted terminal amino group at the surface of the same or a different secondary particle. Subsequent heating at temperatures of 150-200° C. promotes imidization giving a thermo-oxidatively stable cross-link. Incorporation of a tri-

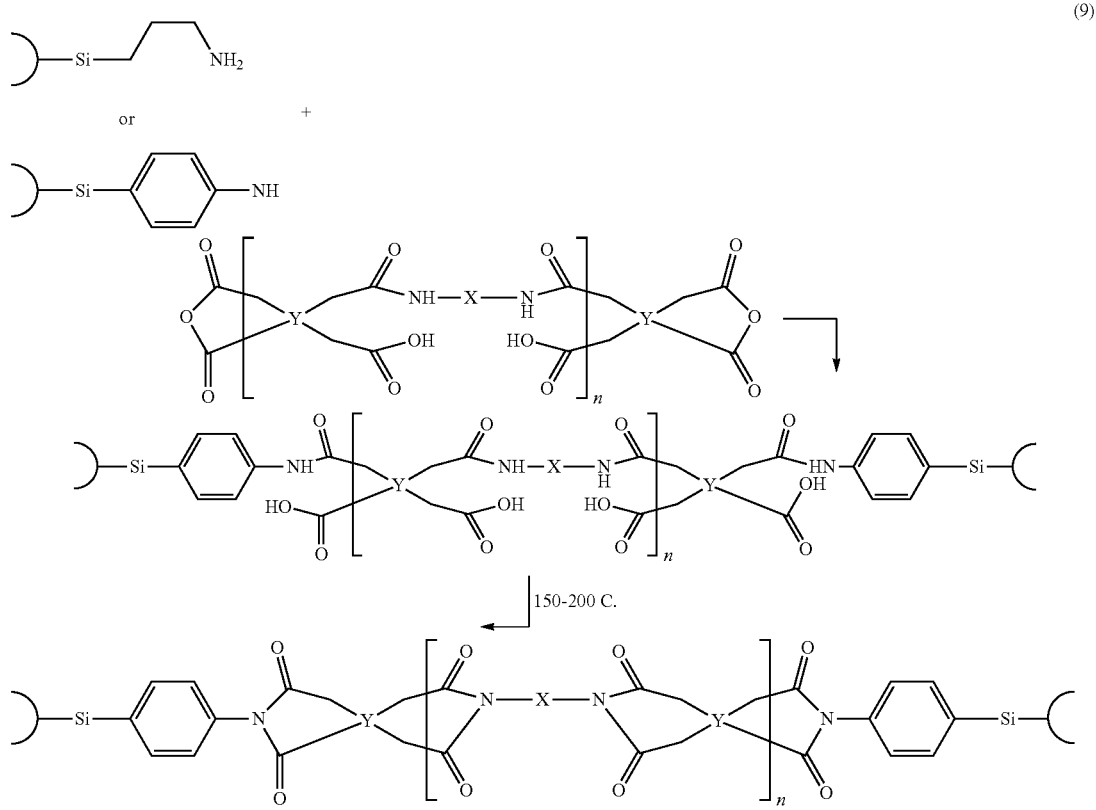

(9)

Examples of X and Y:

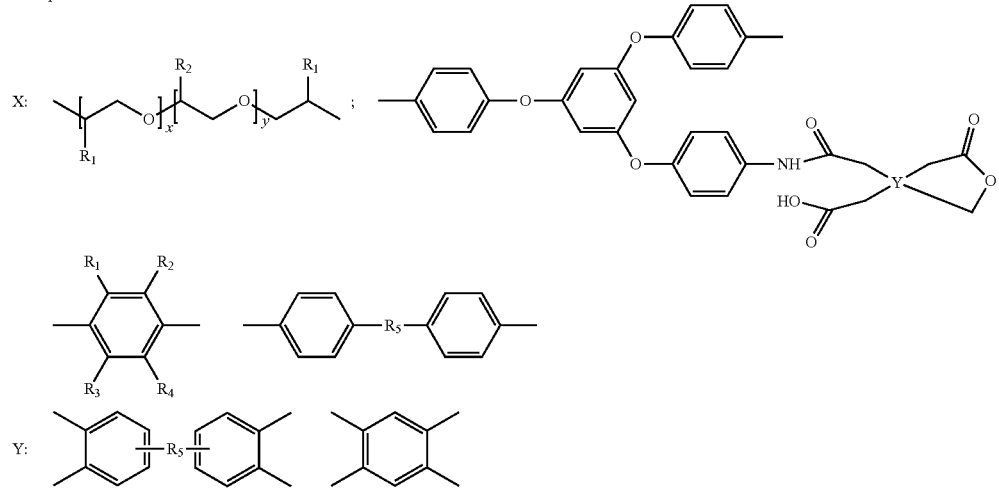

$R_1$ = H, $CH_3$, $CF_3$, alkyl, phenyl; $R_2$ = H, $CH_3$, $CF_3$, alkyl, phenyl;
$R_3$ = H, $CH_3$, $CF_3$, alkyl, phenyl; $R_4$ = H, $CH_3$, $CF_3$, alkyl, phenyl;
$R_5$ = nil, carbonyl, hexafluoroisopropylidene, methylene, oxygen;
$R_6$ = nil, carbonyl, hexafluoroisopropylidene, methylene, oxygen functional amine in the polyamic acid as shown in Eq. 10 allows n attachments of surface amines to anhydrides along oligomer backbones.

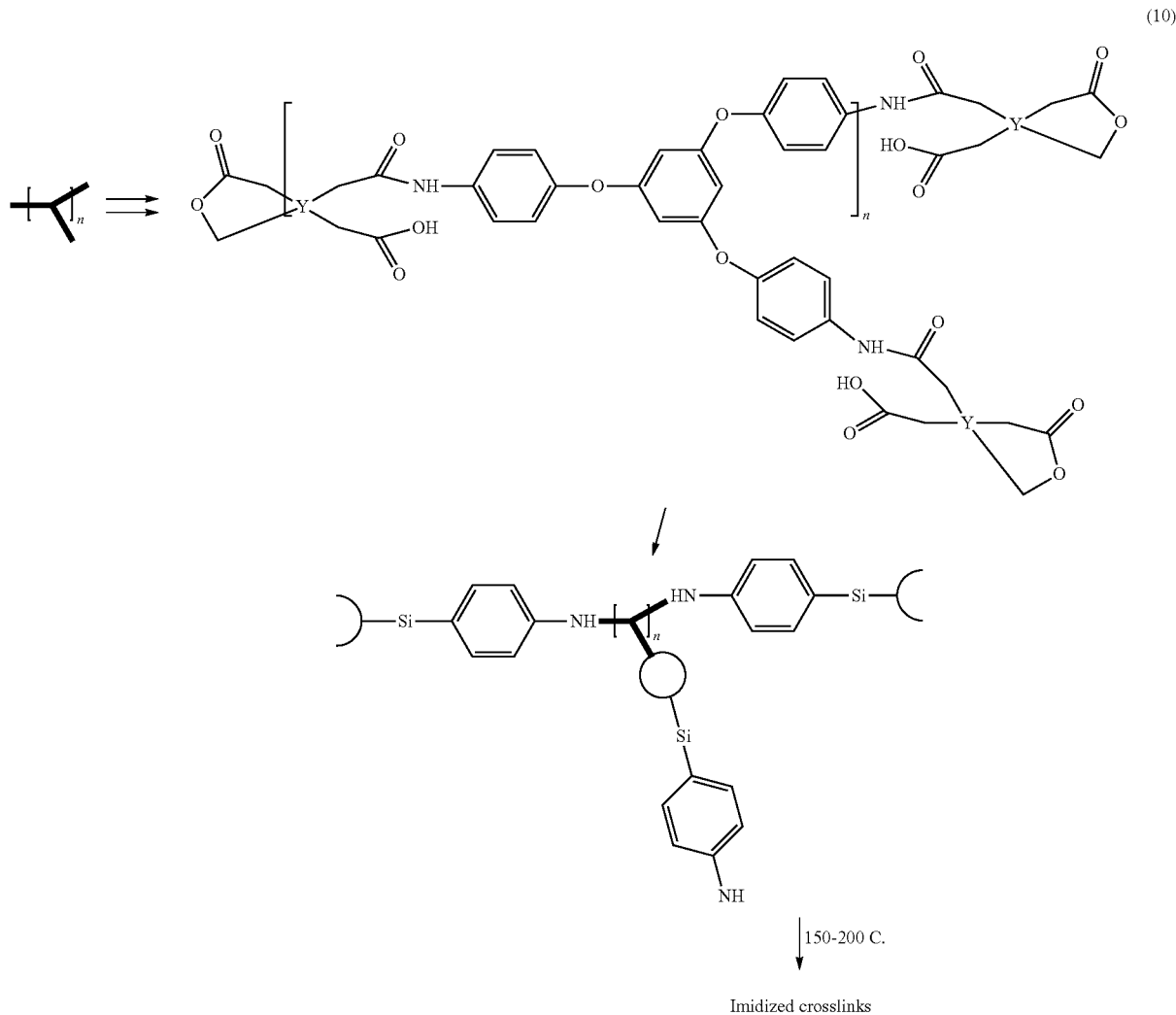

(10)

Imidized crosslinks

In addition to cross-linking the ceramic oxide via the isocyanate-, epoxy- and styrene-based polymer chains described above, other polymer architectures also could be used for cross-linking. The first step will be to select an appropriate base species or monomer to be attached to the ceramic oxide to support the desired polymer architecture. For example, a moiety including a free carboxylic acid group can be attached to the ceramic oxide if it is desired to produce a polyester cross-linking architecture. Alternatively, other functional groups also could be decorated to the ceramic oxide network, such as other olefins (polyolefin cross-linking architecture), alkyl or aryl halides (polybenzoxazole cross-linking), ketones or aldehydes (polybenzimidazole cross-linking), ethers (polyether cross-linking), etc. It should be evident that once the appropriate base or monomeric species has been decorated to the ceramic oxide network's internal surfaces, cross-linking is a matter of performing essentially the conventional cross-linking reactions, using conventional reaction conditions, associated species (such as catalysts and initiators), solvents, etc., with care taken to select conditions, solvents, etc. compatible with the solid ceramic oxide network. However, except for terminal hydroxyl groups, ceramic oxides are highly stable, inert materials, so there will be few instances where selection of appropriate cross-linking species and/or conditions will be impacted by the particular ceramic oxide sol gel to be polymer cross-linked.

It also will be evident that attachment of the desired base or monomeric species to the ceramic oxide network, e.g. to decorate the particle surfaces of such network with the functional groups that will support the desired cross-linking chemistry, will be a matter of routine based on the present disclosure. Broadly, one selects or designs a molecule having the desired reactive species to support cross-linking via the desired architecture, but also having another reactive site that can be used to attach the molecule (having the reactive species) to the ceramic oxide network. In the case of amine-decorated silica as above, the mentioned functional group is an amine, and the other reactive site is an (or more than one) alkoxysilane(s), e.g. three ethoxysilyl groups on APTES. Alternatively, if the native hydroxyl groups on ceramic oxide surfaces are to be used, then the reactive site should be reactive with such terminal hydroxyl groups to produce an analogous result. It will be understood that the cross-linking supportive functional group and the other reactive site to attach the molecule to the ceramic oxide network can be the same (as for the polyfunctional epoxides described above), or they can be different (as for 4-vinylbenzyl chloride, also described above).

In addition to the polymerizable moieties on the monomeric species used to cross-link the surface-bound functional groups either present or incorporated into a ceramic oxide network, such species also can have other chemical moieties effective to impart a desired property to the finished polymer cross-linked ceramic oxide aerogel composition. For example, any of the aforementioned monomeric species (epoxides, styrenes and isocyanates), as well as other monomeric species capable to support other cross-linking architectures, can have, e.g., attached phosphate group(s), which are known to impart flame retardant qualities to materials. As a further example, conducting polymers having free valence electrons capable to act as charge carriers can be incorporated into the monomeric species to impart a degree of electrical conductivity to the finished aerogel. As a still further example, catalytic species also can be incorporated in this manner. Other groups or moieties capable to impart other desired physical, chemical, electrical, magnetic, non-linear optical or other properties also can be incorporated in this manner, which incorporation would be within the ability of a person having ordinary skill in the art. Such groups that can be so incorporated into the polymer cross-linked aerogels through incorporation in monomeric (polymerizable) species used for cross-linking are broadly referred to herein as 'additive functional groups' because they impart added characteristics to the final aerogel. Alternatively, such groups can be added either by post-gellation treatment, or by post-cross-linking treatment with appropriate attachable molecules.

It is to be noted that numerous other species, moieties and/or side groups may be incorporated into the monomers that produce the selected polymer cross-linking architecture, similar to those described above for the flex-link precursors. For example, fire-retardant or other side-groups may be incorporated so that the polymer conformal coating will possess desirable properties and impart them to the overall aerogel. Similar considerations as mentioned above with respect to tuning the flexible linkages also will apply when designing and/or selecting appropriate cross-linking mononers and architecture. For example, while the flexible linkages described above can affect the flexibility of the underlying ceramic-oxide network, a degree of additional flexibility can also be introduced into the polymer conformal coating described here.

A mixture of different monomeric species having different overall structures also can be used to produce the polymer cross-linking structure for an aerogel so long as the different monomers have common or compatible polymerizable moieties; e.g. a styrene moiety or an epoxy moiety, etc. For example, the degree of flexibility of a polymer cross-linked ceramic oxide aerogel will depend, among other things, on the prevalence of rotatable bonds in the cross-linked polymer structure. Much rotation is possible for carbon-carbon or carbon-heteroatom single bonds in a polymer chain. Alternatively, higher order (double or triple) carbon-carbon bonds, a high degree of cross-linking as well as aromatic rings in the polymer chain do not permit significant rotation. Consequently, a polymer network composed primarily of highly cross-linked isocyanate (polyurea), or based on highly unsaturated monomers (significant degree of higher order bonds), will produce a relatively rigid, inflexible cross-linking structures. If it is nonetheless desired to produce a more flexible cross-linking structure, apart from the flexibility that is introduced to the underlying aerogel skeleton via the flex-links mentioned above, then a mixture of polyisocyanate monomers, e.g. one monomer having few or no rotatable bonds and another having longer chains between cross-links, can be used, and their ratio tuned to achieve a desired degree of flexibility in the cross-linked polymer structure. Of course, the total available range of available flexibility may be constrained within broad limits based on the cross-linking architecture selected, but some degree of adjustment should be possible through this technique.

Conversely, a cross-linked network based on epoxy chains, having numerous ether linkages, which permit a high degree of rotation, will be substantially more flexible, and its flexibility may depend on the proportion of ether linkages in the network. Still further, ether linkages can be provided in other, non-epoxy monomers, such as polyisocyanate monomers or polyimides using amine terminated polyalkyleneoxides in the polymer chain as shown in Eq. 9 above, to impart a greater degree of flexibility to the resulting cross-linking architecture as described above. At this point, it should be evident that a person having ordinary skill in the art will be able to design a wide variety of cross-linking architectures, based on a variety of polymerizable species, additive functional groups, other structural linkages and moieties within the polymerizable species, etc., to produce aerogels having characteristics suitable to any number of potentially desirable applications. There is virtually no limit to the applications for the potential variety of polymer cross-linked ceramic oxide aerogels that could be prepared by a skilled person based on the present disclosure.

The polymer cross-linking described above imparts a conformal coating over the surfaces of the secondary particles of the ceramic network. This coating has been shown to improve the mechanical strength of the finished and dried ceramic aerogels, but it does not improve the flexibility of the underlying ceramic-oxide network. To improve flexibility of the underlying aerogel the flexible linkages described above are also incorporated by providing appropriate flexible linkage precursors into the synthesis reaction mixture as above described. As will by now be appreciated, according to this approach both flexible linkages and a polymer cross-linked conformal coating anchored to native —OH and/or non-native functional groups can be incorporated directly into the pearl-necklace strands of secondary particles.

While the foregoing descriptions have been provided with respect to a silica network, the above cross-linking methods and methods to incorporate flex-links are not to be limited to silica, as the methods and reactions described herein to produce a cross-linked ceramic oxide and ceramic oxides having greater flexibility are also applicable to other ceramic oxides. For example, the methods and reactions described herein also could be used to produced other polymer cross-linked ceramic oxides, and ceramic oxides with improved flexibility, including but not limited to titania, vanadia, manganesia, zirconia, ruthenia, alumina, iron oxide, india (indium oxide), yttria, europia, etc., (which can be represented as $TiO_x$, $VO_x$, $MnO_x$, $ZrO_x$, $RuO_x$, $AlO_x$, $FeO_x$, $InO_x$, $YO_x$, $EuO_x$, etc., respectively). All of these ceramic oxides will have terminal hydroxyl groups present on internal surfaces thereof, which form the respective ceramic oxides and define their mesoporous networks. Accordingly, all of these, as well as other ceramic oxides, can be cross-linked as described herein by using the surface-bound hydroxyl groups to attach the desired moiety to support the chosen cross-linking architecture. Alternatively, other ceramic oxides besides silica also can be produced having non-hydroxyl functional groups decorated to the internal surfaces thereof. Specifically, such other ceramic oxides can be produced via appropriate reactions analogous to the TMOS-APTES hydrolysis reaction for producing amine-decorated silica, with suitable ceramic oxide precursors based on the associated metallic or semimetallic element, "Z," having leaving groups attached to a central Z atom via reactive or reaction-labile bonds, and functional groups attached via non-reactive or non-reaction-labile bonds. For example, an alkoxy-Z and a functionalized $ZO_x$ precursor species, (a generic ceramic oxide being represented as $ZO_x$), having at least one functional group attached to the Z-atom via a non-reactive bond can be prepared by persons having ordinary skill in the art for the desired metallic or nonmetallic "Z" atom, and copolymerized via a sol gel process employing an appropriate reaction for producing a gelled ceramic oxide network decorated with the desired functional group. Alternatively, the ceramic oxide mesoporous network can be decorated with appropriate functional groups by post-gellation treatment with molecules having the desired functional groups that will support cross-linking via the desired chemistry, but also having another reactive site that can be used to attach the molecule (having the reactive species) to the ceramic oxide network, or one containing flex linkages and exhibiting improved flexibility as described herein. In that regard, such reactive site that can be used to attach said molecule to the ceramic oxide network can be based on the same metallic or semimetallic element "Z" as the ceramic oxide mesoporous network, or another element. For example, the mesoporous surfaces of a metallic or semimetallic ceramic oxide mesoporous network can be decorated with amines by post-gellation treatment with APTES, or it can be modified with styrene by post-gellation treatment with p-trimethoxysilyl styrene.

In addition, the flex-links mentioned herein, or analogous ones based on other metallic or semi-metallic elements, could likewise be incorporated into ceramic oxides based on other metallic or semi-metallic elements using the methodology herein described. For example, whereas the flex link precursor to be incorporated into the synthesis reaction for a silica aerogel may be:

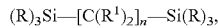

$(R)_3Si—[C(R^1)_2]_n—Si(R)_3$, the analogous molecule may be incorporated into the synthesis reaction (with or without retained $R^1$ groups as described above) for other ceramic oxides, wherein Si is simply replaced by the corresponding metallic or semi-metallic element.

It is expected that not all metal and semimetal oxide mesoporous networks will be amenable to all these methods, and it is recognized and expected that some experimentation may be necessary to determine whether functionalized wet gel networks based on other, non-Si metallic or semimetallic elements can be prepared via sol gel chemistry to produce a gelled solid network. In addition, some ceramic oxides may require acid or base catalysis, different reaction conditions such as high temperature for endothermic reactions, low temperature for highly exothermic reactions, appropriate solvents, etc. However, such experimentation is well within the ability of a person having ordinary skill in the art, and will be routine based on the present disclosure once the desired ceramic oxide, the functional groups to be decorated thereto and the flex-link species have been identified for producing an aerogel with the desired properties. While some experimentation may be necessary to identify appropriate flexible linkages and precursors for them in a specific case, this will be within the capabilities of a person of ordinary skill in the art who has reviewed the present disclosure. For example, a matrix may be set up containing a variety of different proposed flex-link precursors for a particular ceramic aerogel, wherein individual candidate flex links have variable chain lengths, degrees of unsaturation, side groups, ether linkages, aromatic character, etc. Through routine testing, optimization of a ceramic oxide aerogel having appropriate flex-link character could be achieved, and appropriate flex links identified.

Regardless of whether any polymeric architecture is used to provide polymeric cross-linking, and of what ceramic oxide is employed, once the wet gel with flexible linkages is formed (and cross-linked) the next step is to remove the liquid (solvent) from that network to produce a dried aerogel. Conventionally, aerogels are prepared from the corresponding wet gel via a $CO_2$ exchange and supercritical drying procedure as described previously. While a polymer cross-linked conformal coating as described has been shown to improve aerogel strength, it has still been necessary to dry the cross-linked gels via the supercritical $CO_2$-mediated process, or in limited cases via solvent exchange through multiple steps to low-surface-interactive solvents such as pentane, to avoid pore-structure collapse and shrinkage as described above. As will become evident in one of the following examples, the incorporation of flexible linkages as herein described into a silica aerogel has been shown to permit air drying of the wet gel into its dried aerogel state without the use of supercritical $CO_2$ or solvent exchanges to special solvents and without any perceptible shrinkage or pore collapse. Accordingly, the combination of a polymer cross-linked aerogel that also includes flexible linkages as described herein is believed to simultaneously meet two distinct needs with respect to making aerogels more robust for commercial and industrial applications:

1. The conformal polymer coating imparts greater strength to the aerogels, making them strong enough to withstand mechanical loads they are likely to encounter during use; and
2. The flexible linkages impart greater flexibility, enabling the wet gels to be air dried without expensive and time-consuming supercritical $CO_2$ methodologies, as well as enabling the dried aerogels to withstand cyclic or opposing mechanical stresses or loads while lowering the risk of brittle fracture.

Certainly, aerogels incorporating both a polymeric conformal coating and flexible linkages as herein described have been shown to exhibit high mechanical strength and, simultaneously, substantial green strength prior to cross-linking as well as improved flexibility and a substantially reduced tendency for brittle failure after cross-linking, as the following examples demonstrate.

In a preferred embodiment, a ceramic oxide network as herein described (such as a silica network) includes both flexible linkages and a polymeric coating linked to surface-bound non-hydroxyl functional groups. In the case of a silica network, the co-hydrolysis of greater than 50 wt. % total a) functionalized silica precursor species (e.g. VTMS or APTES) and b) flexible linkage precursor species (e.g. BTMSH), with the balance being unfunctionalized silica precursor, wherein all weight percentages are based solely on the total silanes present, can produce dried aerogels that exhibit a significant degree of recovery following compressive strain. When the total of functionalized silica precursor species and flexible linkage precursor species is above 66% (based on total silanes), almost total recovery of compressive strain following compression has been observed for certain dried aerogels. Preferably, the ceramic-oxide network is prepared from 50-100 wt. % total functionalized precursor species and flexible-linkage precursor species, wherein the reaction mixture includes at least 10 wt. % (more preferably at least 12 wt. %, 14 wt. % or 16 wt. %) flexible-linkage precursor and at least 1 wt. % (more preferably at least 5 wt. % or 10 wt. %) functionalized ceramic-oxide precursor species. In case the total of flexible-linkage precursor species and ceramic-oxide precursor species do not sum to 100 wt. % of total silanes, the balance is unfunctionalized ceramic-oxide precursor species, which does not include moieties retained on the metallic/semi-metallic element following the network-synthesis reactions. Most preferably, the total of functionalized ceramic-oxide precursor species and flexible-linkage precursor species is at least 66 wt. %, balance (if any) unfunctionalized ceramic-oxide precursor species. In the case of a silica network, an exemplary embodiment includes 0-90 wt. % unfunctionalized silica precursor species (e.g. TMOS, TEOS), and 50-100 wt. %, more preferably 66-100 wt. %, total functionalized silica precursor species (e.g. APTES, VTMS) and flexible-linkage precursor (e.g. BTMSH, bis(trimethoxysilylpropyl)amine).

Further aspects of the present invention will be illustrated and understood in the context of the following examples, which are provided by way of illustration and not limitation.

EXAMPLE 1

Polystyrene Cross-linked Aerogels with 1,6-Bis(trimethoxysilyl)hexane Flex-Link

An experiment was performed to incorporate flexible linkages into a functionalized aerogel, wherein vinyl functionality was also incorporated at the secondary particle surfaces and used as an anchor to support polystyrene cross-linking of the aerogel. Thus, the resulting aerogel incorporated both flexible linkages and a polymer cross-linked conformal coating as described herein. Numerous samples were prepared to demonstrate the effect of varying the reactant concentrations on the resulting aerogel properties. To prepare the gels, first the following components were combined in a reaction mixture using ethanol as the solvent to carry out the network-synthesis reaction via hydrolysis and condensation:
tetramethoxysilane (TMOS), which is an unfunctionalized silica gel precursor species wherein all Si— bonds are hydrolysable;
1,6-bis(trimethoxysilyl)hexane (BTMSH) as the flexible linkage precursor, wherein the flexible linkage portion consists of a hexane chain linked at either end to silicon atoms whose other three valences are bound to methoxy groups via hydrolysable bonds; and
vinyltrimethoxysilane (VTMS), which is a functionalized silica gel precursor species having vinyl functionality linked to the central Si atom via a non-hydrolysable bond, and three methoxy species also linked via hydrolysable bonds.

The structures of these reactants are provided below.

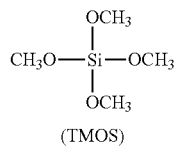
(TMOS)

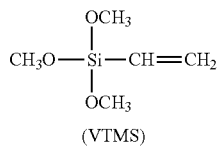
(VTMS)

$(CH_3O)_3$—Si—$(CH_2)_6$—Si—$(OCH_3)_3$
(BTMSH)

The total moles of silane (the sum of all three of the above components) were varied from 0.44 mol/l to 1.90 mol/l as shown in Table 1. The amount of VTMS was varied from 22.85 to 57.05 mol % of the total silane. The amount of BTMSH flex-link precursor was varied from 0 to 34.21 mol % of the total silane. The water:silane mole ratio ranged from 7.5 to 8.7 depending on the composition (water is the hydrolysis reactant). Ammonium hydroxide ($NH_4OH$) was used to catalyze the hydrolysis reactions and was kept constant at 1.00 ml for every 100 ml solution of the final mixture. For each sample, the silica gels were prepared by combining the three silane components with water and catalyst in the proportions listed below in table 1. In Table 1, only the mol percentages of BMTSH and VTMS are given, with the understanding that the balance of total silane in each sample is TMOS.

As a typical example, sample 21 from Table 1 was prepared from 1.37 mol/L of total silane, wherein the total silane included 32.83 mol % BTMSH, 38.30 mol % VTMS and balance TMOS. To prepare each sample, each of the silane components was provided from a solution of that component in methanol or ethanol, wherein the silane-source solutions were mixed in appropriate proportions to achieve the total moles silane and the silane concentrations reported in Table 1. The resulting mixed silane solution was cooled to below 0° C. in an acetone dried ice bath. A basic solution consisting of 1.00 ml $NH_4OH$, balance water was then added to each mixed silane solution so that each reaction mixture totaled 100 ml. The resulting reaction mixtures were thoroughly mixed together before being poured into 20-ml plastic syringe molds. Wet gel monoliths formed within 15 minutes to 1 day, and were aged for 24 hours. After aging, the gels were extracted into fresh MeOH or EtOH and allowed to rest for 24 hours. The gels were washed once more with fresh MeOH or EtOH and then solvent-exchanged to chlorobenzene in three wash steps.

The resulting wet gels, now in chlorobenene solution, were polymer cross-linked as follows. Styrene solution was prepared from a 50/50 wt % solution of styrene monomer in chlorobenzene. Final formulated molecular weight (MW), ranging from 1000 to 5000 g/mol, was controlled by the number of moles of polymerization initiator, 2,2'-Azobis(2-methylpropionitrile) (AIBN), that was introduced. All gels were soaked in the styrene mixture for 3 days, and then washed with fresh chlorobenzene, followed by heat treatment at about 70-75° C. for 24 hours. After heating, the gels were again washed with chlorobenzene twice before solvent exchanging with acetone. The cross-linked gels were then supercritically dried with liquid carbon dioxide ($CO_2$). Measured physical properties of each dried aerogel monolith are also provided in Table 1.

TABLE 1

Preparation conditions and some measured properties of the styrene cross-linked aerogel monoliths.

| Run No. | Total silane | BMTSH, mol % (based on total silane) | VTMS, mol % (based on total silane) | Styrene, FMW | Density, mg/cm³, of dried aerogel | Porosity, %, of dried aerogel | Modulus, MPa, of dried aerogel | % non-recoverable strain of dried aerogel |
|---|---|---|---|---|---|---|---|---|
| 1 | 1.26 | 17.87 | 23.78 | 3000 | 326.84 | 76.78 | 17.54 | 9.5 |
| 2 | 0.95 | 31.55 | 52.58 | 5000 | 175.37 | 85.90 | 0.47 | 1.55 |
| 3 | 1.68 | 0 | 41.67 | 1000 | 329.93 | 76.64 | 20.35 | 10 |

TABLE 1-continued

Preparation conditions and some measured properties of the styrene cross-linked aerogel monoliths.

| Run No. | Total silane | BMTSH, mol % (based on total silane) | VTMS, mol % (based on total silane) | Styrene, FMW | Density, mg/cm³, of dried aerogel | Porosity, %, of dried aerogel | Modulus, MPa, of dried aerogel | % non-recoverable strain of dried aerogel |
|---|---|---|---|---|---|---|---|---|
| 4 | 1.61 | 0 | 24.9 | 5000 | 326.65 | 77.33 | 20 | 9.5 |
| 5 | 1.75 | 0 | 57.01 | 1000 | 277.47 | 79.83 | 12.62 | 9.3 |
| 7 | 0.84 | 17.85 | 23.83 | 5000 | 440.86 | 68.30 | * | * |
| 8 | 1.37 | 32.83 | 38.3 | 5000 | 232.25 | 82.32 | 3.29 | 0.45 |
| 9 | 1.37 | 32.83 | 38.3 | 5000 | 241.02 | 81.65 | 1.07 | 1.95 |
| 10 | 1.75 | 17.1 | 39.92 | 3000 | 284.4 | 78.36 | 10.68 | 8.15 |
| 11 | 0.95 | 31.55 | 52.58 | 3000 | 172.46 | 86.19 | 0.23 | 2.65 |
| 12 | 0.88 | 34.2 | 22.83 | 1000 | 149.72 | 88.66 | 0.34 | 14.7 |
| 13 | 0.88 | 34.2 | 22.83 | 1000 | 236.96 | 82.26 | 2.78 | 12.4 |
| 14 | 1.68 | 17.86 | 23.8 | 1000 | 369.62 | 70.58 | 32.43 | 11.1 |
| 15 | 1.75 | 34.21 | 22.8 | 3000 | 312.97 | 76.58 | 6.28 | 4.55 |
| 16 | 1.2 | 0 | 24.88 | 1000 | 315.55 | * | * | * |
| 17 | 1.75 | 34.21 | 22.8 | 5000 | 318.02 | 76.40 | 7.32 | 3.55 |
| 18 | 0.91 | 16.41 | 54.71 | 1000 | 121.99 | 90.34 | 0.17 | 0.99 |
| 19 | 1.83 | 16.41 | 54.71 | 5000 | 228.13 | 83.28 | 1.67 | * |
| 20 | 0.84 | 17.85 | 23.83 | 5000 | 308.89 | 77.89 | 18.04 | 6.7 |
| 21 | 1.37 | 32.83 | 38.3 | 1000 | 241.75 | 81.15 | 2.42 | 1 |
| 22 | 1.37 | 32.83 | 38.3 | 1000 | 249.67 | 80.92 | 0.87 | 1.3 |
| 24 | 1.61 | 0 | 24.9 | 5000 | 330.55 | * | * | * |
| 26 | 1.83 | 16.41 | 54.71 | 5000 | 237.3 | 82.16 | 1.75 | 1.5 |
| 29 | 1.32 | 0 | 57.03 | 3000 | 280.95 | 79.28 | * | * |
| 30 | 0.91 | 16.41 | 54.71 | 1000 | 124.64 | 90.33 | 0.2 | 8.4 |

* Not measured

Figure 6:
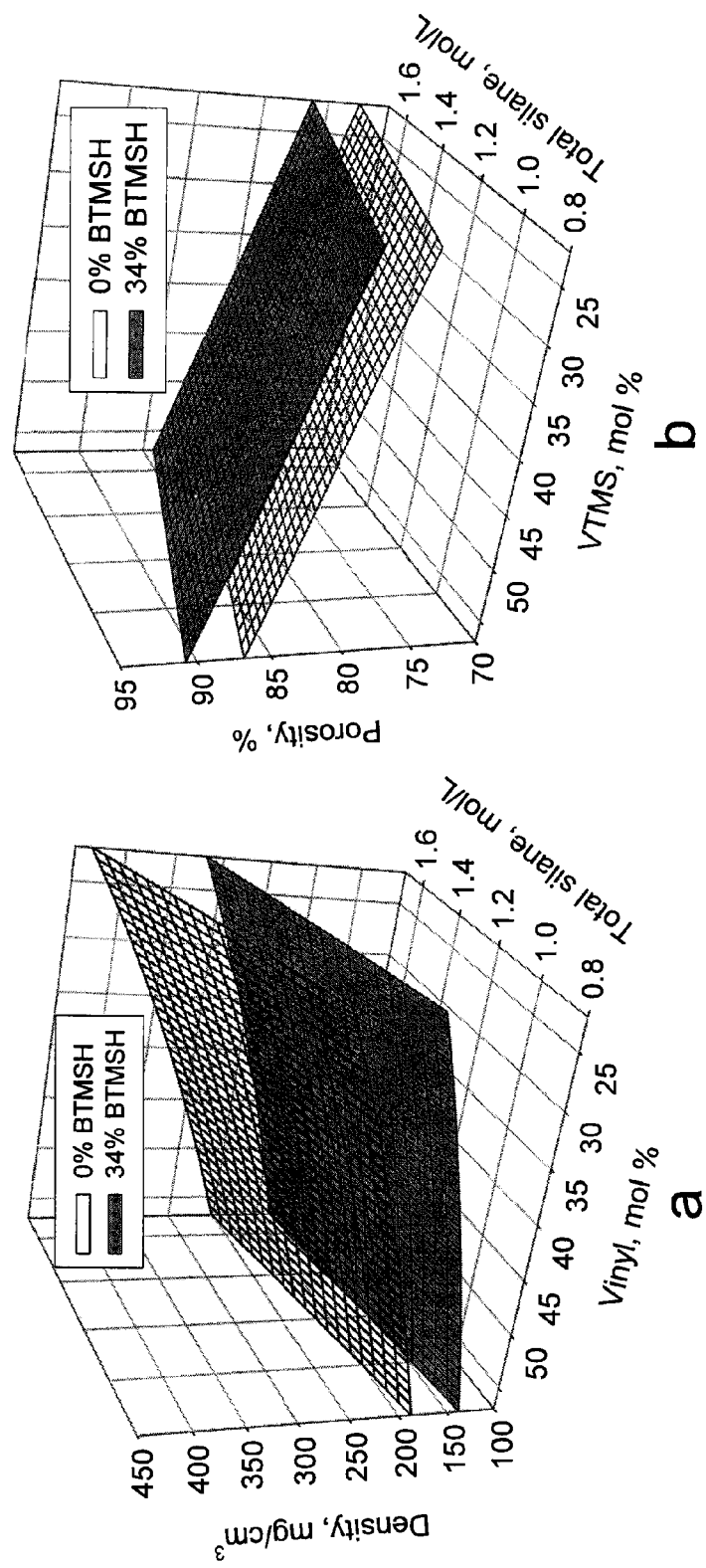
FIG. 6 consists of response surface models showing a) density and b) porosity of aerogel monoliths prepared in Example 1 graphed vs. VTMS and total silane concentration.

Data from Table 1 was analyzed using multiple linear regression analysis to create empirical models representing the relationships between the variables and the measured responses, with selected results shown in FIG. 6. In that figure, the clear response surfaces represent predicted density or porosity of aerogels incorporating 0% flex-links (bi-silylhexyl linkages), and the shaded response surfaces represent predicted density or porosity of aerogels incorporating 34% BTMSH flex-links. Plots of the resulting response surface models for density graphed vs. total silane and VTMS concentration are shown in FIG. 6a. Density of the monoliths increased with increasing total silane and VTMS, and decreased with increasing amounts of BTMSH. Increasing amounts of VTMS would tend to increase the amount of cross-linking while BTMSH would limit the amount of cross-linking. The porosity versus total silane and VTMS concentration data, shown in FIG. 6b, show that increasing amounts of total silane and VTMS reduced porosity, while porosity increased with increasing amounts of BTMSH. Also according to the model, styrene formulated molecular weight had no significant effect on density or porosity.

Figure 7:
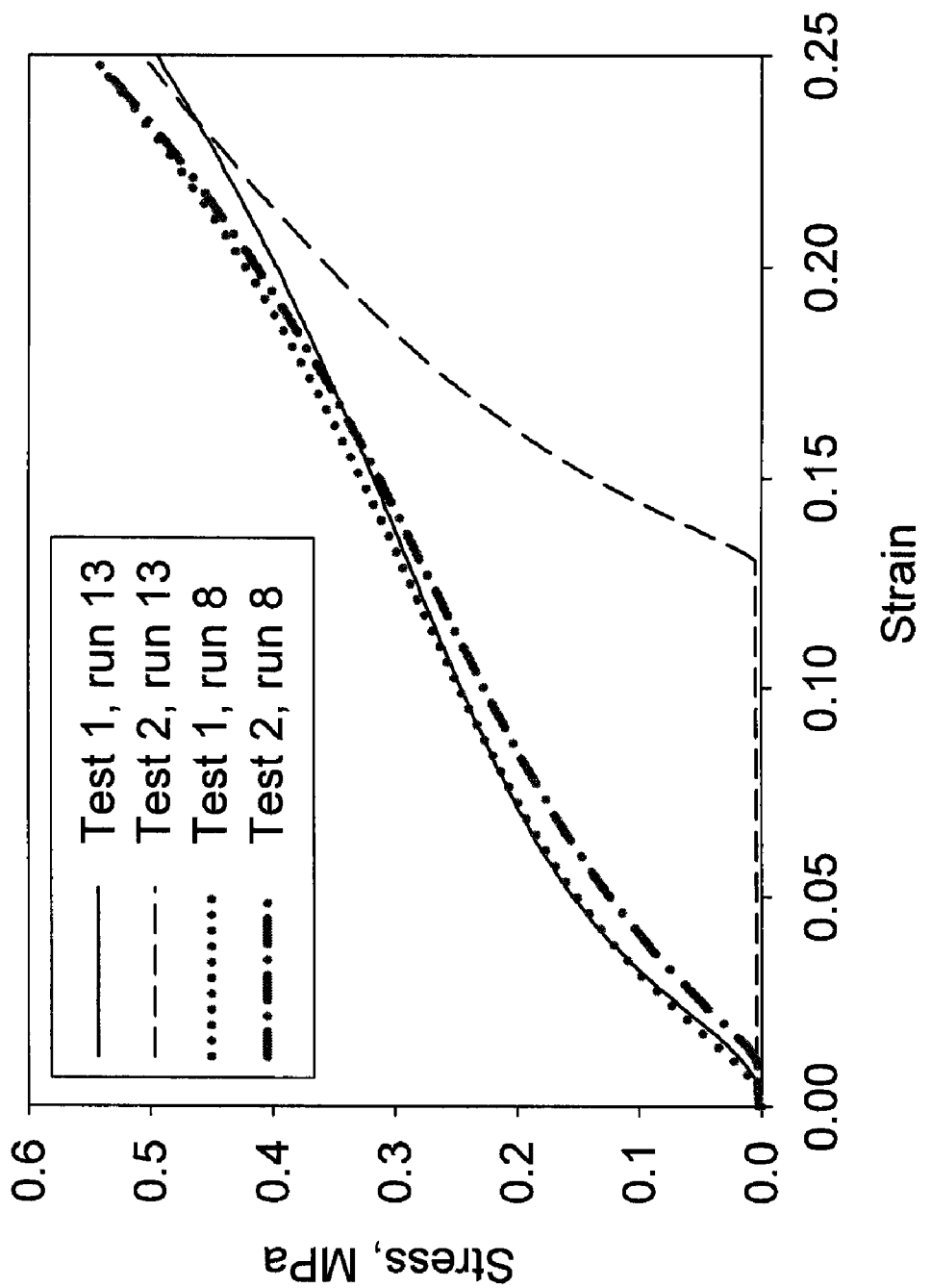
FIG. 7 shows compression curves for two separate aerogels, samples 13 and 8 respectively, from Example 1 that showed a similar modulus. Sample 13 only recovered halfway, while sample 8 showed almost complete recovery from compression.

As evident from Table 1, compression tests were carried out on the aerogel monoliths. In addition, the amount of unrecoverable compressive strain, a typical test for measuring flexibility of foams, was also measured on the monolith samples. In the typical compression-deflection test, a sample was compressed to 25% strain and released twice. After a fixed time (in this case 30 minutes), the length of the sample was measured. The value of unrecoverable compressive strain is given in Table 1 as the percent of the length that did not recover for each monolith. Stress-strain curves for compression for a couple of the runs from Table 1 having similar moduli are shown in FIG. 7. Note that the compression curves (black) from test 1 and test 2 for the monolith from run 13 show that around 12.4% of the strain was unrecoverable, while those from run 8 (red) almost perfectly overlapped showing almost all strain was recoverable up to 25%. Note also that since the compression tests were done in rapid succession, the stress-strain curves indicate that the recovery of sample after the first compression was almost instantaneous.

Figure 8:
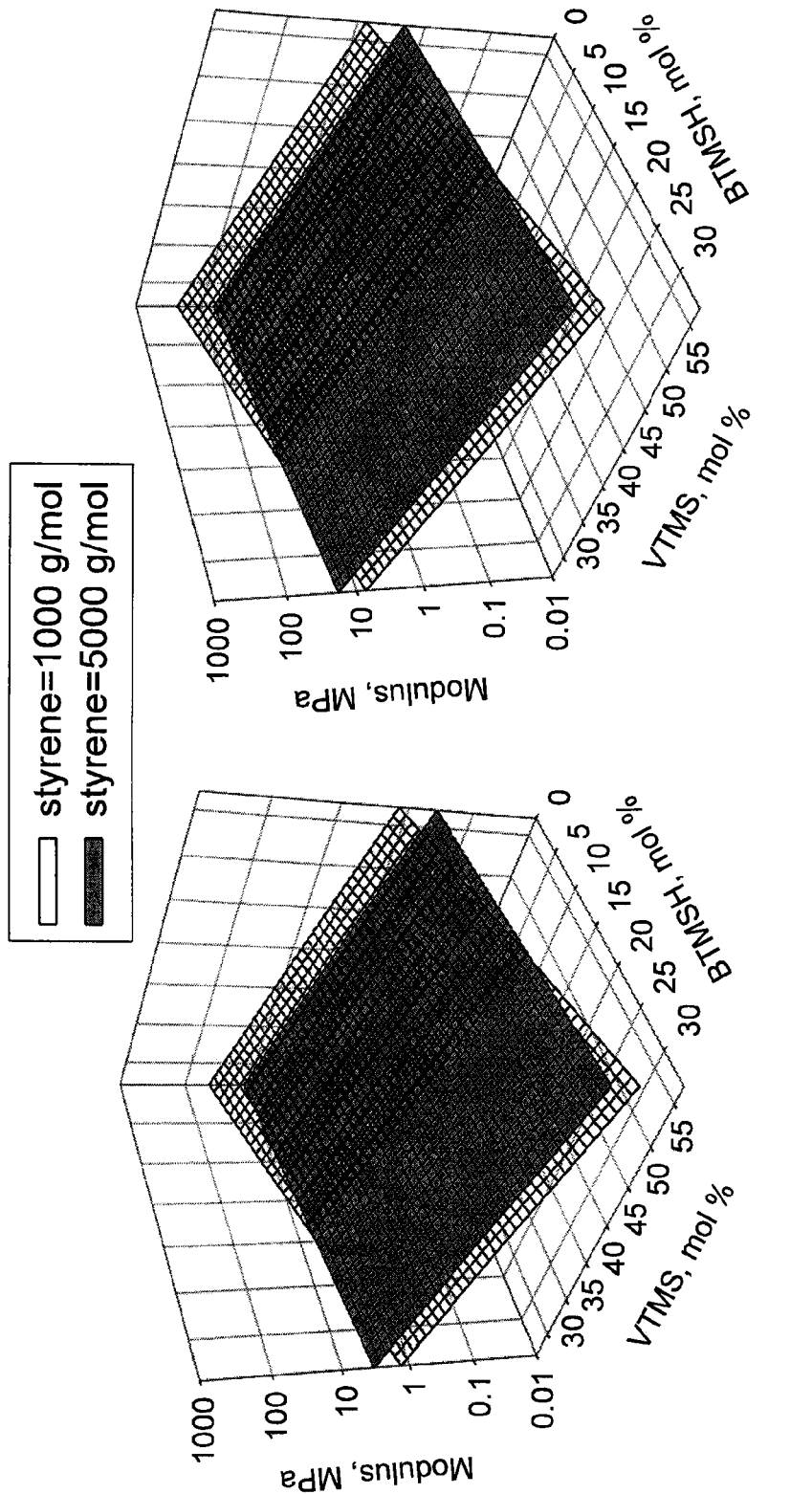
FIG. 8 shows fitted models of modulus from compression data of aerogel monoliths from Example 1 a) when total silane=0.84 mol/l and b) when total silane=1.75 g/mol graphed vs. VTMS and BTMSH fraction.

Data from compression tests were also modeled using multiple linear regression analysis. FIGS. 8a (total silane=0.84 mol/l) and 8b (total silane=1.75 mol/l) show the modulus from compression graphed vs. VTMS and BTMSH concentrations at different levels of styrene MW and total silane concentration. Modulus was significantly dependent on all four variables. Increasing total silane concentration caused an increase in modulus, while increasing VTMS and BTMSH concentration decreased modulus. There appeared to be a synergistic effect of BTMSH concentration and the styrene molecular weight. Increasing BTMSH concentration caused modulus to decrease much more when styrene MW was set to 1000 (clear surfaces), while at styrene MW set to 5000 (gray surfaces), the decrease in modulus from 0% to 34% BTMSH was much smaller.

Figure 9:
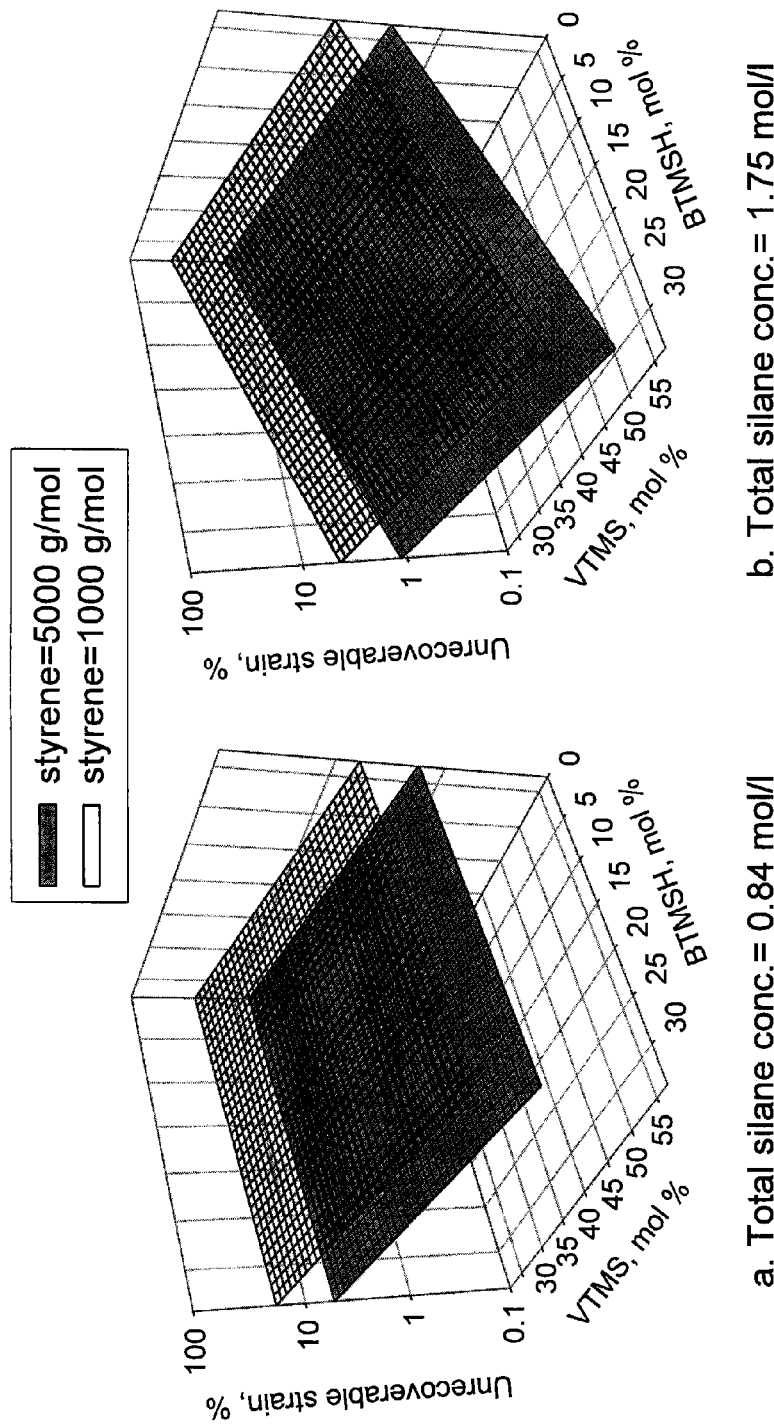
FIG. 9 shows fitted models of unrecoverable strain from compression-deflection tests of aerogel monoliths from Example 1 a) when total silane=0.84 mol/l and b) when total silane=1.75 g/mol graphed vs. VTMS and BTMSH fraction.

Graphs of response surface models for unrecoverable compressive strain are shown in FIG. 9a (total silane=0.84 mol/l and 9b total silane=1.75 mol/l). Again, unrecoverable compressive strain was significantly dependent on all four variables. Unrecoverable compressive strain always decreased with increasing VTMS concentration and increasing styrene MW. When total silane concentration was low, unrecoverable compressive strain slightly decreased with increasing BTMSH concentration, while the effect was much more pronounced when total silane concentration was high. The lowest predicted values for unrecoverable compressive strain occurred with total silane at 1.84 mol/L, VTMS concentration (based on total silane) at 57 mol %, BTMSH concentration (based on total silane) is 34 mol % and styrene MW at 5000. Monoliths made using this combination of conditions should recover almost entirely after being compressed to 25% strain. Also evident from the graphs, it is not enough to use BTMSH in high concentrations to get almost full recovery. Rather, a combination of BTMSH and VTMS in at least 50 mol % of the total silane was needed when total silane and styrene FMW are at a high to get non-recoverable strain to 1% or less.

At least 66 mol % was needed when total silane was at a low and styrene high. When both styrene FMW and total silane concentration were low, nonrecoverable strain was never lower than 5.5%.

Thus, the physical properties of the silica aerogel were varied based on varying the concentrations of the reactants for making the gel, (functionalized, unfunctionalized and flex-link precursor silane species) and correspondingly the degree of cross-linking and flex-linkage incorporation in the resulting aerogel.

EXAMPLE 2

Air Dried Aerogels that Exhibit No or Negligible Shrinkage or Fracture

Figure 10:
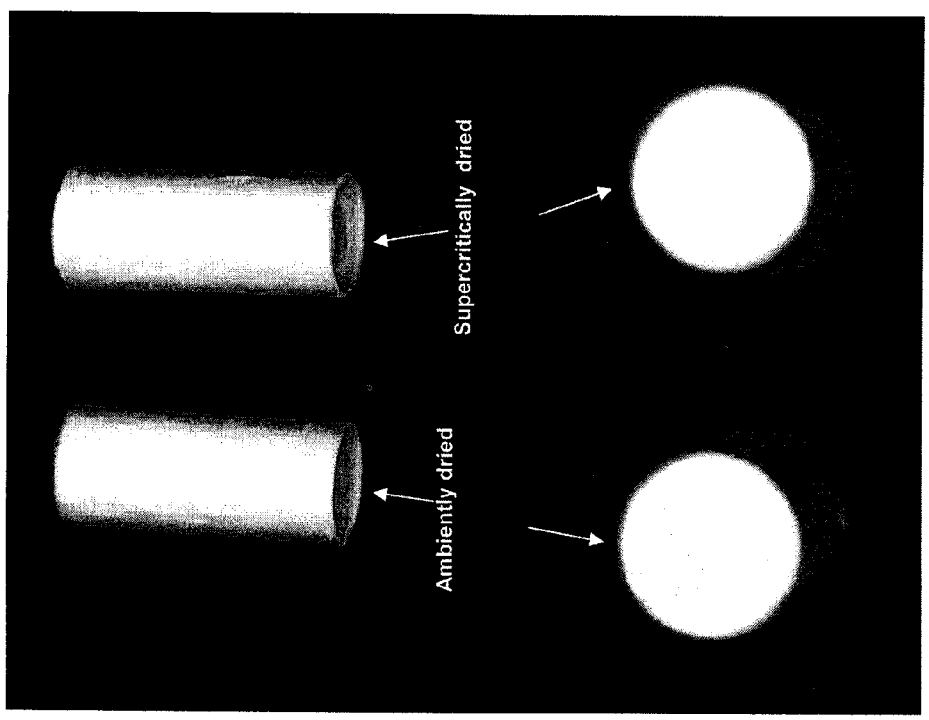
FIG. 10 is a photograph showing two silica aerogels having the same composition and incorporating flexible linkages as described in Example 2. One of the aerogel monoliths was dried in ambient air and the other via the conventional supercritical $CO_2$-mediated process. No appreciable shrinkage was observed in the air-dried sample.

Typically, conventional aerogels require supercritical fluid extraction of the solvent in order to maintain the gel's porous network in the final product. Ambiently dried gels ("xerogels") typically collapse and shrink, giving a much more dense material. However, it has been observed that by adding 30-50 mol % of a flex-link additive, gels can be air-dried at ambient pressure without observable shrinkage or fracture. Specifically, two monoliths were prepared similarly as in Example 1 above, wherein the total silane included 32.83 mol % BTMSH as the flex-link precursor, 36.3 mol % VTMS as the functionalized silica precursor and balance TMOS as the unfunctionalized silica precursor, in 1.37 mol/L total silane. One of the monoliths was dried using the conventional supercritical $CO_2$-mediated drying procedure, wherein the reaction solvent is exchanged with liquid $CO_2$, which is then converted directly into the supercritical state. The other monolith was allowed to dry in room air at atmospheric (ambient) pressure, with no special drying treatment. The two samples are shown in FIG. 10, wherein the sample on the left was ambiently dried and the sample on the right was dried via the supercritical $CO_2$ process. As can be clearly observed, both of the samples have similar size and density, indicating that no appreciable shrinkage occurred in the air-dried monolith.

EXAMPLE 3

Di-Isocyanate Cross-Linked Aerogels with 1,6-Bis(Trimethoxysilyl)Hexane as Flexible Link Use of a flex-link in the underlying silica gel backbone is also demonstrated using a combination of TMOS, BTMSH and APTES with a di-isocyanate monomer (Desmodur N3200) used to produce polymeric cross-linking from amine groups at the secondary-particle surfaces. The structures of the three silane species are reproduced below for convenience.

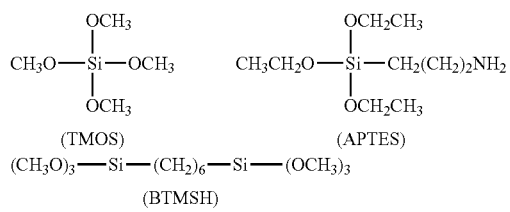

(TMOS)   (APTES)

$(CH_3O)_3$—Si—$(CH_2)_6$—Si—$(OCH_3)_3$
(BTMSH)

The total moles of silane (the sum of the above three components) were varied from 0.25 M to 0.75 M as shown in Table 2. The amount of APTES was held constant at 17.5 mol % while BTMSH was varied from 10 to 50 mol % of the total silane. The balance total silane in each sample was thus TMOS. The amount of di-isocyanate was varied from 10 to 30 w/w % of solution. The water:silane mole ratio was held constant at 7 for each reaction.

TABLE 2

Preparation conditions and some measured properties of the di-isocyanate cross-linked aerogel monoliths

| run | BTMSH, mol %, based on total silane | Total silane, mol/L | N3200 conc. w/w % | Bulk Density g/cc |
|---|---|---|---|---|
| 1 | 50 | 0.75 | 30 | 0.204 |
| 2 | 30 | 0.5 | 20 | 0.092 |
| 3 | 30 | 0.5 | 20 | 0.097 |
| 6 | 10 | 0.25 | 10 | 0.036 |
| 7 | 10 | 0.25 | 30 | 0.053 |
| 8 | 30 | 0.75 | 20 | 0.155 |
| 10 | 30 | 0.25 | 20 | 0.027 |
| 12 | 10 | 0.5 | 20 | 0.086 |
| 13 | 30 | 0.5 | 20 | 0.086 |
| 15 | 50 | 0.25 | 30 | 0.021 |
| 18 | 30 | 0.5 | 30 | 0.099 |
| 19 | 30 | 0.5 | 10 | 0.080 |

The silica gels were prepared by combining a solution of the three silane components with water. No additional catalyst was required as APTES provided sufficient base functionality to catalyze hydrolysis. To prepare the reaction mixture for each sample, the three silane components were combined according to the respective proportions for each sample in acetonitrile solvent and the mixed silane solution then was cooled to below 0° C. in an acetone dried ice bath. Water was then added to the cooled mixed silane solution to make up a total of 100 ml reaction mixture for each sample. The resulting mixtures were thoroughly mixed together before being poured into 20-ml plastic syringe molds. Wet gel monoliths formed within 15 to 30 minutes, and were aged for 24 hours. After aging, the gels were extracted into fresh AcN and allowed to rest for 24 hours. The gels were washed three more times with fresh AcN. The gels were then soaked in a 30 w/w % N3200 di-isocyanate for 24 hours, washed with fresh AcN, and heated at about 70° C. for 24 hours. After heating, the gels were washed with AcN three times before supercritical drying with carbon dioxide ($CO_2$).

Figure 11:
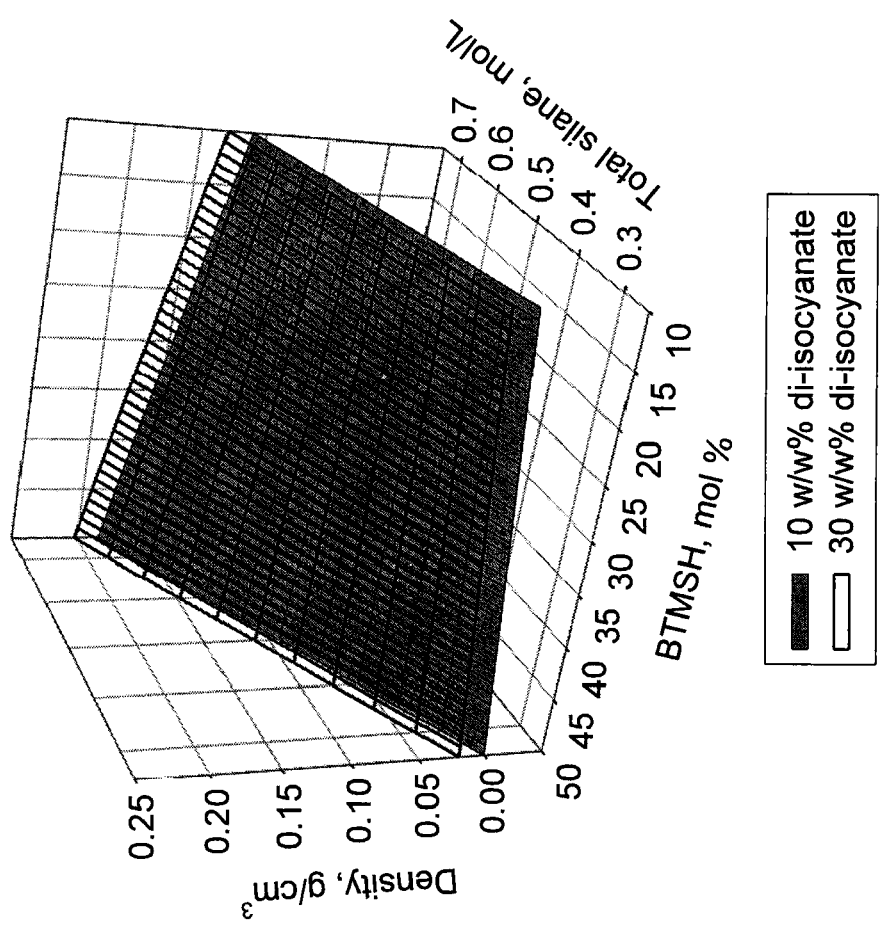
FIG. 11 is a graph of a response surface model for density vs. total silane and BTMSH concentration based on the aerogel samples made in Example 3.

Densities of each monolith were measured, and density data was modeled using multiple linear regression analysis. Plots of the resulting response surface models for density graphed vs. total silane and BTMSH concentration are shown in FIG. 11. As seen in the figure, density increased with increasing total silane and di-isocyanate concentration. Furthermore, when total silane concentration was low (0.25 mol/L), density decreased with increasing amounts of BTMSH, while at high total silane, density increased with increasing amounts of BTMSH.

Figure 12:
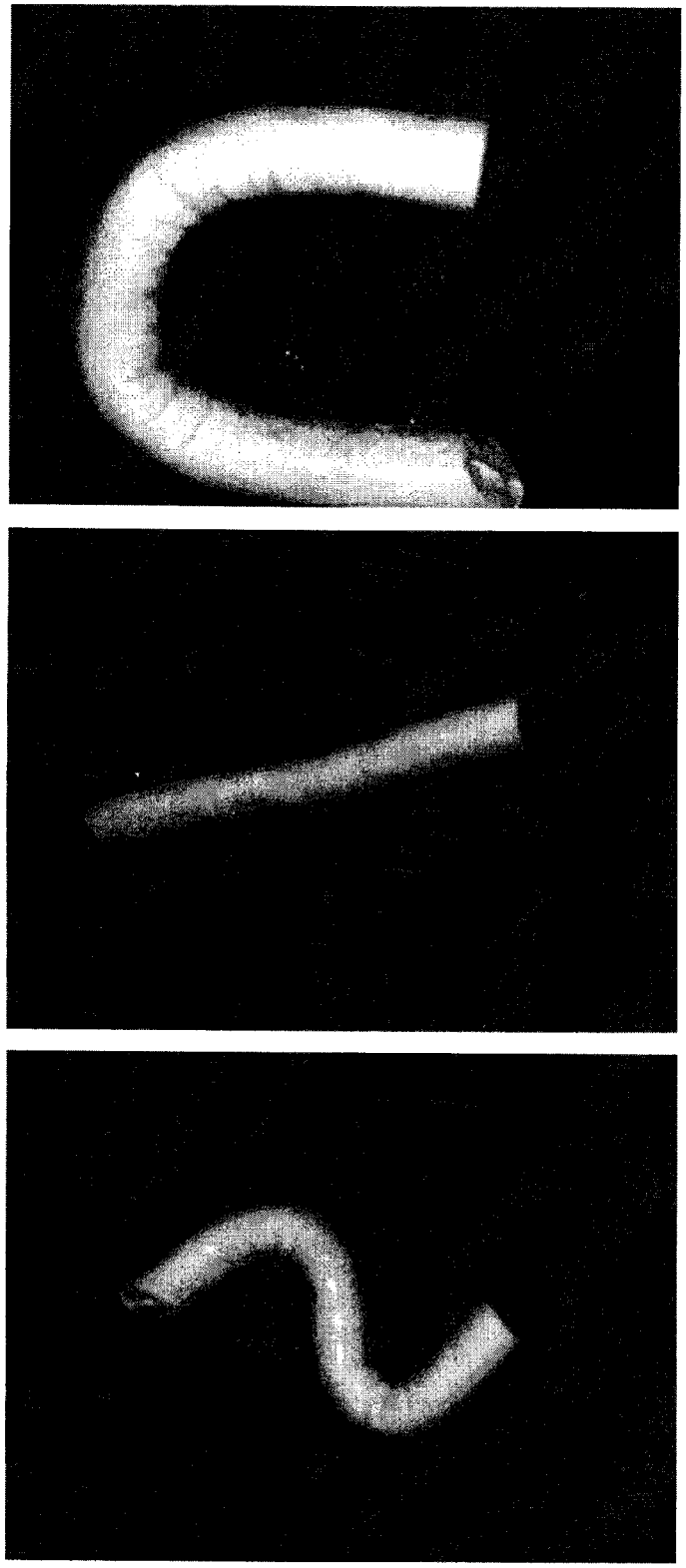
FIG. 12 shows photographs of silica wet gels prepared as described in Example 3, which exhibited a high degree of flexibility and could be manipulated by hand and bent into various conformations without breaking.

Though mechanical properties were not measured for the di-isocyanate cross-linked aerogels, handling the monoliths suggested that those containing high concentrations of the flex-link additive exhibit recoverable compression comparable to the styrene cross-linked aerogels described in Example 1 above. In addition, wet gels before cross-linking were easier to handle, resulting in less breakage on extraction from molds. FIG. 12 shows wet silica gels made from a formulation similar to run 8 in this Example, prior to drying. As can be clearly seen from the figure, the gels exhibited a surprising amount of flexibility and could be bent and manipulated into various conformations without breaking.

EXAMPLE 4

Polyurethane Cross-Linked Aerogels with Bis-(Trimethoxysilylpropyl)-Amine as Flexible Linkage In this example, Bis(3-trimethoxysilylpropyl)amine, BTSPA, was used as both underlying flex-link and amine reactive site. Table 3 shows results of different formulations of silica aerogels, cross-linked with N3300A. The structures of both BTSPA and Desmondur N3300A are shown below.

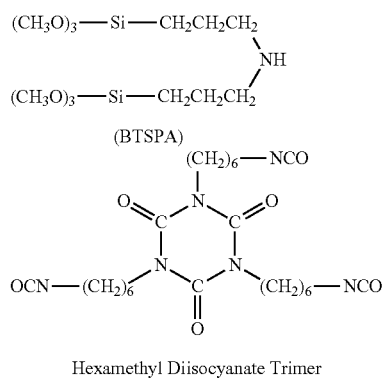

Hexamethyl Diisocyanate Trimer

For each sample in this Example, the appropriate mixture of BTSPA and TMOS (if any) in acetonitrile (ACN) was prepared to produce the compositions referenced in Table 3, and cooled to below 0° C. in an acetone dried ice bath. Thereafter, water was added to effect hydrolysis and condensation. The contents were thoroughly mixed before being poured into molds. Gelation occurred within minutes, and wet gels were aged for 24 hours. Once extracted, the gels were washed in acetonitrile four times before the cross-linking reaction was carried out.

Incorporating the flex link itself improved the handle-ability of the uncross-linked gels before drying compared to gels with no flex-link. However, after supercritical drying, non-crosslinked gels tended to fall apart very easily. To cross-link the gels, they were soaked in a 30 w/w % solution of Desmodur N3300A, a trifunctional isocyanate, in acetonitrile for 24 hours, followed by heat treatment at 75° C. for 6 hours in fresh acetonitrile. The resulting cross-linked gels were washed 4 times with acetonitrile, and then supercritically dried with liquid $CO_2$. After drying, elastic modulus and compression data were measured for each monolith and values are reported in Table 3.

TABLE 3

Aerogel monoliths containing BTSPA flex-link and cross-linked with N3300A.

| Exp. | Total Si, mol/L | TMOS, mol % | BTSPA, mol % | Density, mg/cm3 | Modulus, MPa | Unrecoverable strain, % |
|---|---|---|---|---|---|---|
| A | 1.52 | 86.53 | 13.47 | 222.40 | 5.88 | 9.80 |
| B | 0.86 | 86.76 | 13.24 | 91.56 | 0.33 | 8.70 |
| C | 0.33 | 86.86 | 13.14 | 55.82 | 0.23 | 8.20 |
| D | 0.8 | 0.00 | 100 | 456.72 | 28.76 | 0.7 |
| E | 0.42 | 0.00 | 100 | 181.18 | 4.04 | 0.3 |

As can be seen from the data, aerogels prepared from 100 mol % BTSPA, with no unfunctionalized silica gel precursor at all, produced aerogels with greater elastic recovery (lowest unrecoverable strain) compared to aerogels made with only 13 mol % BTSPA.

Figure 13:
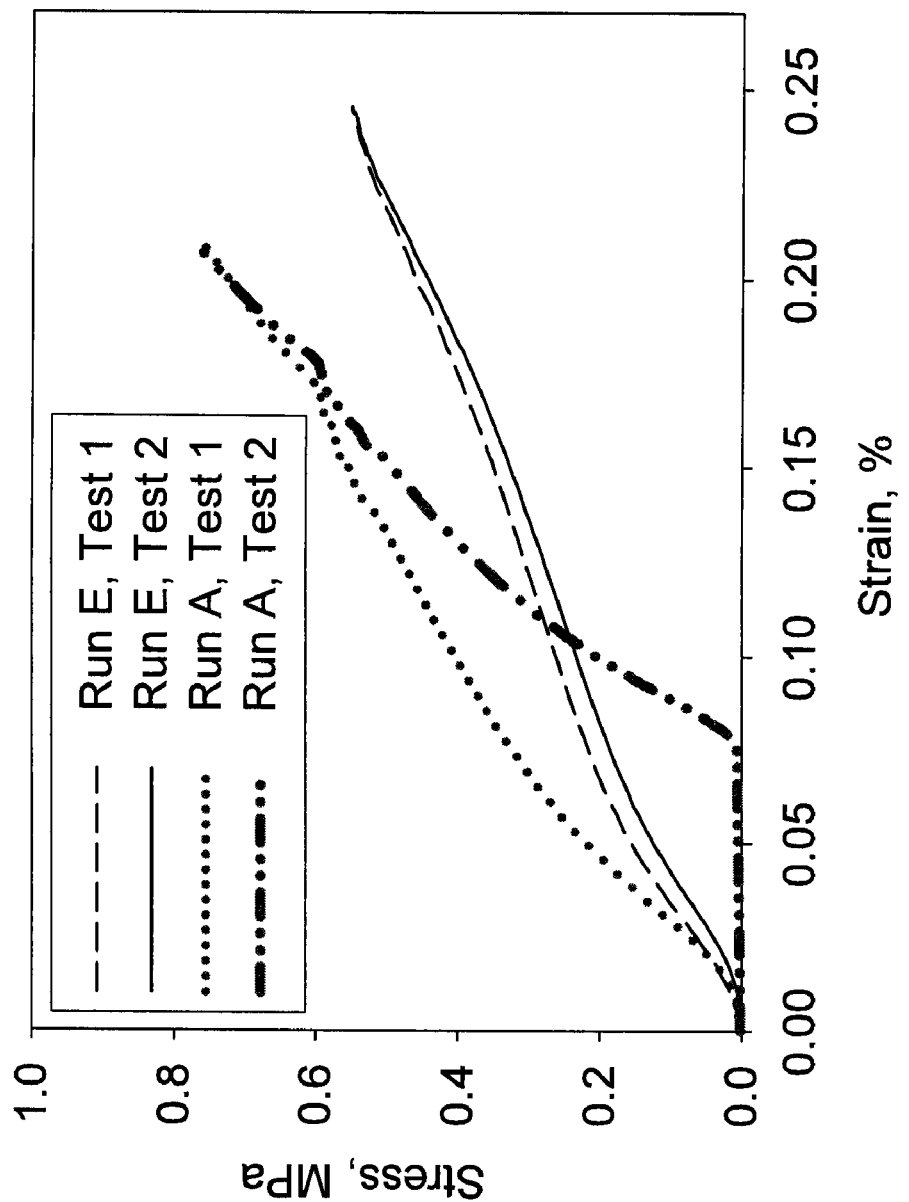
FIG. 13 shows compression curves for two separate aerogels, Runs A and E respectively, from Example 4 comparing the degree of recoverability between them based on their respective BTSPA concentrations (~13% versus 100% of total silanes).

To illustrate, stress-strain curves for Run A (13.47% BTSPA) and Run E (100% BTSPA) are shown and compared in FIG. 13. Though Runs A and E had similar compressive moduli, Run A exhibited 9.8% unrecoverable strain while Run E nearly completely recovered when compressed to 25% strain. An optimization study using intermediate values of BTSPA with TMOS and higher total silane may allow for optimized samples with similar recovery and higher modulus as seen in the previous Examples.

As the above Examples demonstrate, the silica aerogels (and the corresponding wet gels) exhibit various physical properties (e.g., elastic modulus) that can be tuned through judicious selection of appropriate starting concentrations of the silane species used to synthesize the gels. In addition, the degree of additional strength and aerogel density can be varied by the degree of polymer cross-linking, which in turn may be regulated by the concentration of non-native functional groups incorporated at the secondary-particle surfaces as cross-link anchors, depending on the selected cross-linking chemistry. Based on the foregoing teachings, a person of ordinary skill in the art will be led to numerous alternative embodiments not expressly disclosed herein but which fall within the scope of the invention and the present teachings. For example, it is expected that other aerogels besides those based on silica could be used, with flexible versions thereof prepared according to analogous methods as those disclosed herein. In addition, alternative flexible linkages may be selected, having varying degrees of chain length, functionality, etc., all of which may be used to tune the degree of flexibility or other desirable properties of a finished aerogel. The concentrations of the silane starting materials (both functionalized and unfunctionalized ceramic oxide precursors, as well as the flex link precursor species) also can be varied to achieve varying degrees of resulting physical properties. It is also contemplated that multiple (i.e. more than one) species of flex link precursor species may be incorporated, which will introduce flexible linkages of different chemistry and structure. These and other variations from the embodiments disclosed herein will be apparent to the person having ordinary skill in the art.

Although the hereinabove described embodiments of the invention constitute the preferred embodiments, it should be understood that modifications can be made thereto without departing from the scope of the invention as set forth in the appended claims.

What is claimed is:

1. A ceramic-oxide network comprising a backbone of interconnected strands of first particles of ceramic oxide, and a plurality of flexible linkages dispersed, but not necessarily uniformly distributed in said backbone of said network, said flexible linkages linking adjacent ones of said first particles thereby segmenting said interconnected strands, said flexible linkages having the form

-M-L-M- wherein:
M is a metallic or semi-metallic element common to the ceramic oxide network; and
L comprises a chain linkage between the opposing M atoms that has the form —[X(R$^2$)$_2$]$_n$— wherein:
X is a carbon atom in the chain between the opposing M atoms;
each $R^2$ is independently selected from the group consisting of hydrogen, substituted or unsubstituted alkyl groups, and substituted or unsubstituted aryl groups; and
n is a positive integer equal to or lower than 10.

2. The ceramic-oxide network of claim 1, said ceramic-oxide network being a silica network wherein M is Si.

3. The ceramic-oxide network of claim 2, at least one $R^2$ in said flexible linkage comprising a reaction site effective as an anchor for polymer cross-linking said network.

4. The ceramic-oxide network of claim 2, wherein L further comprises an atom other than C in the chain between the opposing M atoms.

5. The ceramic-oxide network of claim 2, wherein n is equal to or lower than 6.

6. The ceramic-oxide network of claim 5, at least one $R^2$ in said flexible linkage comprising a reaction site effective as an anchor for polymer cross-linking said network.

7. The ceramic-oxide network of claim 5, wherein L further comprises an atom other than C in the chain between the opposing M atoms.

8. The ceramic-oxide network of claim 1, said flexible linkages having the form —Si-L-Si— and being provided from at least one flexible-linkage precursor selected from the group consisting of:

9. The ceramic-oxide network of claim 1, said flexible linkages having the form —Si-L-Si— wherein L comprises aromatic functionality.

10. The ceramic-oxide network of claim 1, said first particles having an average particle size greater than 5 nm and being made up of agglomerations of relatively smaller, tightly-packed second particles of ceramic-oxide having a particle size less than 2 nm, wherein said interconnected first-particle strands, segmented by said flexible linkages, define a mesoporosity of said ceramic-oxide network.

11. The ceramic-oxide network of claim 1, further comprising non-hydroxyl functional groups bound to surfaces of said first particles, said network of ceramic oxide particles being cross-linked via organic polymer chains that are attached to said first particles via reaction with at least a portion of said surface-bound non-hydroxyl functional groups.

12. The ceramic-oxide network of claim 11, said organic polymer chains being in the form of a substantially conformal polymer coating over said first-particle strands.

13. The ceramic-oxide network of claim 11, said flexible linkages comprising amine groups attached thereto, said organic polymer chains being further attached to said amine groups.

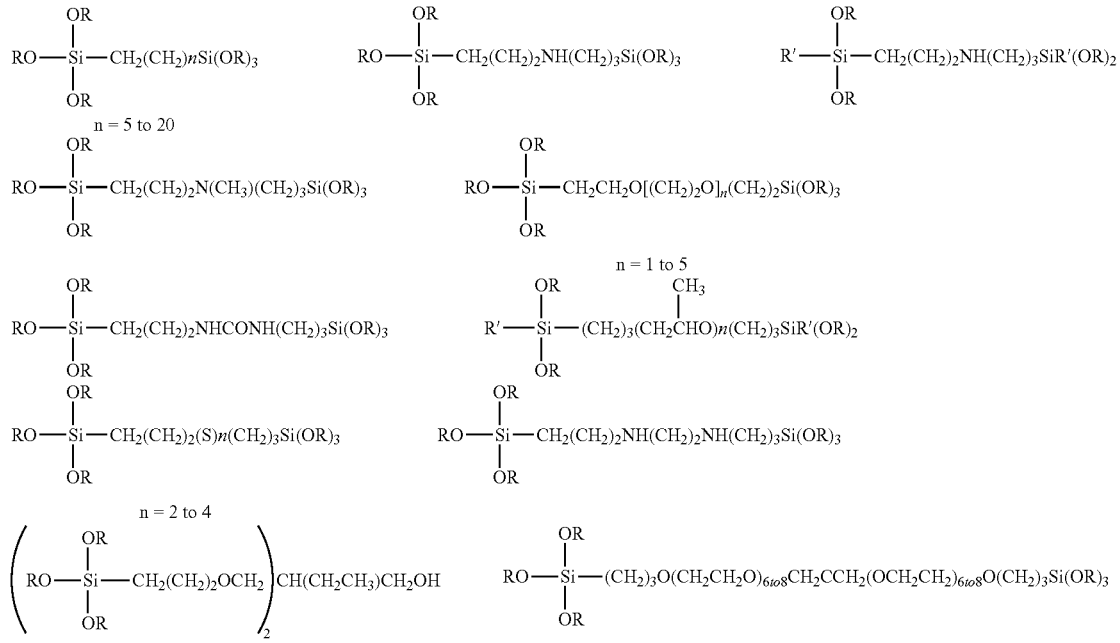

wherein each R and R' in each of the above is individually selected as hydrogen or alkyl, and R's in each of the above are different from Rs attached to the same atom therewith, said flexible linkages being formed through hydrolysis of Si—O bonds in the selected flexible-linkage precursor(s), wherein said flexible linkages are incorporated into said network via attachment of terminal silicon atoms thereof to said first particles via Si—O—Si bonds.

14. The ceramic-oxide network of claim 13, said ceramic-oxide network being a silica network, said flexible linkages having the form

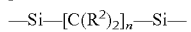

wherein:
n is equal to or lower than 6; and
said amine groups are provided in at least a portion of said $R^2$ groups or attached to Si atoms in said flexible linkages.

15. The ceramic-oxide network of claim 11, said non-hydroxyl functional groups comprising amines.

16. The ceramic-oxide network of claim 11, said organic polymer chains comprising polyurea chains.

17. The ceramic-oxide network of claim 11, said organic polymer chains being provided via copolymerization of at least two distinct monomeric species.

18. The ceramic-oxide network of claim 11, said interconnected first-particle strands defining a mesoporosity of said ceramic-oxide network, wherein the mesoporous network has a volume void fraction of at least 80%.

19. The ceramic-oxide network of claim 18, said volume void fraction being about or at least 95%.

20. The ceramic-oxide network of claim 11, said first particles being silica particles and said surface-bound non-hydroxyl functional groups comprising groups selected from the group consisting of amines and vinyl groups.

21. The ceramic-oxide network of claim 20, said organic polymer chains being in the form of a substantially conformal polymer coating over said first-particle strands, which polymer coating is attached to said first particles via linkages with said surface-bound non-hydroxyl functional groups.

22. The ceramic-oxide network of claim 11, said non-hydroxyl functional groups being selected from the group consisting of amines and vinyl groups.

23. The ceramic-oxide network of claim 1, said network being a silica wet gel that is sufficiently flexible that it can be bent into a plurality of different conformations without breaking.

24. The ceramic-oxide network of claim 1, said network being a silica wet gel produced from a reaction mixture comprising a tetraalkylorthosilicate, 1,6-bis(trimethoxysilyl)hexane as a precursor to said flexible linkages, and water in an organic solvent, said wet gel being produced from said reaction mixture via hydrolysis and condensation reactions.

25. The ceramic-oxide network of claim 1, said flexible linkages each comprising a hexane chain.

26. The ceramic-oxide network of claim 1, wherein n is equal to or lower than 6.

27. The ceramic-oxide network of claim 1, L having the form $$-[C(R^2)_2]_n-$$

wherein n is equal to or lower than 6.

28. The ceramic-oxide network of claim 1, said flexible linkages having the form —Si—(CH$_2$)$_6$—Si—.

29. The ceramic-oxide network of claim 1, said flexible linkages having the form —Si—(CH$_2$)$_3$—NH—(CH$_2$)$_3$—Si—.

30. The ceramic-oxide network of claim 1, said flexible linkages having the form —Si—(CH$_2$)$_3$—S$_n$—(CH$_2$)$_3$—Si—, where n=2 to 4.

31. The ceramic-oxide network of claim 1, said flexible linkages being provided from at least one flexible-linkage precursor comprising:

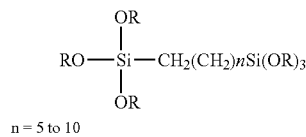

n=5 to 10
wherein each R is individually selected as hydrogen or alkyl.

32. A method of preparing a ceramic-oxide network, comprising copolymerizing a reaction mixture comprising at least one ceramic-oxide precursor species and at least one flexible-linkage precursor through one or a series of chemical reactions to produce said ceramic-oxide network, said at least one ceramic-oxide precursor species comprising a metallic or semimetallic element bound to at least one moiety through a bond that is labile under conditions of said one or a series of chemical reactions, said at least one flexible-linkage precursor having the form $$(R)_y(R^1)_x-M-L-M-(R^1)_{x'}(R)_{y'}$$

wherein:
M is a metallic or semi-metallic element;
each R is attached to the associated M atom via a bond that is labile under the conditions of said reaction(s) and is individually selected to be an alkoxy or other group that will not prevent said reaction(s);
each R$^1$ is attached to the associated M atom via a bond that is not labile under the conditions of said reaction(s) and can be individually selected to be an alkyl group;
L comprises a chain linkage between the opposing M atoms that has the form $$-[X(R^2)_2]_n-$$

wherein X is a carbon atom in the chain between the opposing M atoms;
each R$^2$ is independently selected from the group consisting of hydrogen, substituted or unsubstituted alkyl groups, and substituted or unsubstituted aryl groups; and
n is a positive integer equal to or lower than 10;
x and y are both integers with y being not less than 1, wherein the sum x+y is equal to the valence of M minus 1; and
x' and y' are both integers with y' being not less than 1, wherein the sum x'+y' is equal to the valence of M minus 1.

33. The method of claim 32, said at least one ceramic-oxide precursor species comprising an unfunctionalized ceramic-oxide precursor species, wherein all moieties attached to a metallic or semi-metallic atom thereof are attached via bonds that are labile under conditions of said reaction(s).

34. The method of claim 33, said at least one ceramic-oxide precursor species further comprising a functionalized ceramic-oxide precursor species, wherein at least one moiety comprising a non-hydroxyl functional group is attached to a metallic or semi-metallic atom thereof via a bond that is not labile under conditions of said reaction(s).

35. The method of claim 32, M being a metallic or semi-metallic element common to said at least one ceramic-oxide precursor species.

36. The method of claim 32, said at least one ceramic-oxide precursor species comprising Si as the metallic or semi-metallic element, M being Si, said flexible-linkage precursor having the form:

$$(R)_3-Si-(C(R^2)_2)_n-Si-(R)_3$$

wherein each R is individually selected to be an alkoxy group.

37. The method of claim 36, wherein n is equal to or lower than 6.

38. The method of claim 32, said at least one flexible-linkage precursor comprising 1,6-bis(trimethoxysilyl)hexane.

39. The method of claim 32, further comprising providing non-hydroxyl functional groups over internal surfaces of said network, and linking at least a portion of said non-hydroxyl functional groups with an organic polymer.

40. The method of claim 39, said non-hydroxyl functional groups being selected from the group consisting of amines and vinyl groups.

41. The method of claim 40, said organic polymer comprising a polymer selected from the group consisting of polyurea, polystyrene and epoxy polymers.

42. The method of claim 39, said ceramic-oxide network being a silica network prepared through copolymerizing the following silanes:

50-100 wt. % total of a) functionalized silica precursor species selected from the group consisting of 3-aminopropyl triethoxysilane, vinyltrimethoxysilane and p-trimethoxysilyl-styrene, and b) bi-siloxyl-terminal flexible-linkage precursor species;

balance tetraalkylorthosilicates;

wherein all of the above weight percentages are calculated based only on the total silanes in the reaction mixture.

43. The method of claim 42, said tetraalkylorthosilicates comprising at least one of tetramethylorthosilicate and tetraethylorthosilicate.

44. The method of claim 42, said bi-siloxyl-terminal flexible-linkage precursor species comprising 1,6-bis(trimethoxysilyl)hexane.

45. The method of claim 42, said network being prepared through copolymerizing 66-100 wt. % total of said functionalized silica precursor species and bi-siloxyl-terminal flexible-linkage precursor species.

46. The method of claim 42, wherein a wet gel produced through copolymerizing said silanes exhibits substantial green strength prior to linking said organic polymer to said non-hydroxyl functional groups.

47. The method of claim 32, said ceramic-oxide network being an amine-decorated silica network prepared by reacting an alkoxysilane, 3-aminopropyl triethoxysilane and a bi-siloxyl-terminal flexible-linkage precursor together under hydrolysis conditions to copolymerize them and thereby produce said silica network having amine functionality provided over internal surfaces thereof and flexible linkages dispersed throughout, but not necessarily uniformly distributed in, said network, said flexible linkages linking adjacent silica particles that are arranged in interconnected strands, thereby segmenting said interconnected strands.

48. The method of claim 32, said ceramic-oxide network being an amine-decorated silica network prepared by reacting an alkoxysilane, vinyltrimethoxysilane and a bi-siloxyl-terminal flexible-linkage precursor together under hydrolysis conditions to copolymerize them and thereby produce said silica network having vinyl functionality provided over internal surfaces thereof and flexible linkages dispersed throughout, but not necessarily uniformly distributed in, said network, said flexible linkages linking adjacent silica particles that are arranged in interconnected strands, thereby segmenting said interconnected strands.

49. The method of claim 32, said at least one ceramic-oxide precursor species comprising Si as the metallic or semi-metallic element, M being Si, said flexible-linkage precursor having the form:

$$(R)_3-Si-L-Si-(R)_3.$$

50. The method of claim 32, said ceramic-oxide network being formed through said reaction(s) as a wet gel having a pore structure that is saturated with a liquid solvent in which said reaction(s) was/were carried out, the method further comprising permitting said wet gel to dry through evaporation of said liquid solvent under ambient conditions to produce a dried aerogel, wherein the dried aerogel exhibits no perceptible shrinkage or pore-structure collapse compared to the wet gel.

51. The method of claim 32, said at least one flexible-linkage precursor comprising bis(trimethoxysilylpropyl)amine.

52. The method of claim 32, L having the form $$-[C(R^2)_2]_n-$$

wherein n is equal to or lower than 6.

53. The method of claim 32, said at least one flexible-linkage precursor being 1,6-bis(trialkoxysilyl)hexane.

54. The method of claim 32, said at least one flexible-linkage precursor being bis(trialkoxysilylpropyl)amine.

55. The method of claim 32, said at least one flexible-linkage precursor being bis(trialkoxysilylpropyl)disulfide.

* * * * *

UNITED STATES PATENT AND TRADEMARK OFFICE
CERTIFICATE OF CORRECTION

PATENT NO. : 8,314,201 B2
APPLICATION NO. : 11/948315
DATED : November 20, 2012
INVENTOR(S) : Mary Ann B. Meador and Baochau N. Nguyen It is certified that error appears in the above-identified patent and that said Letters Patent is hereby corrected as shown below:

At Col. 43, Line 66 in Claim 31, delete second instance of "n=5 to 10".

Signed and Sealed this
Twenty-ninth Day of January, 2013

David J. Kappos
*Director of the United States Patent and Trademark Office*